United States Patent
Balbaky et al.

(10) Patent No.: US 12,251,560 B1
(45) Date of Patent: Mar. 18, 2025

(54) CONNECTION QUALITY DETERMINATION FOR WEARABLE NEUROSTIMULATION SYSTEMS

(71) Applicant: Cala Health, Inc., Burlingame, CA (US)

(72) Inventors: Sami Balbaky, San Jose, CA (US); Samuel Richard Hamner, San Francisco, CA (US)

(73) Assignee: Cala Health, Inc., San Mateo, CA (US)

(*) Notice: Subject to any disclaimer, the term of this patent is extended or adjusted under 35 U.S.C. 154(b) by 0 days.

(21) Appl. No.: 16/993,085

(22) Filed: Aug. 13, 2020

Related U.S. Application Data

(60) Provisional application No. 62/886,218, filed on Aug. 13, 2019.

(51) Int. Cl.
*A61N 1/08* (2006.01)
*A61N 1/36* (2006.01)

(52) U.S. Cl.
CPC ........... *A61N 1/08* (2013.01); *A61N 1/36142* (2013.01); *A61N 1/36175* (2013.01); *A61N 2001/083* (2013.01)

(58) Field of Classification Search
CPC .. A61N 1/08; A61N 1/36142; A61N 1/36175; A61N 2001/083
See application file for complete search history.

(56) References Cited

U.S. PATENT DOCUMENTS

| | | | |
|---|---|---|---|
| 3,204,637 A | 9/1965 | Frank et al. | |
| 3,870,051 A | 3/1975 | Brindley | |
| 4,103,808 A | 8/1978 | Hallman et al. | |
| 4,300,575 A | 11/1981 | Wilson | |
| 4,458,696 A | 7/1984 | Larimore | |
| 4,461,075 A | 7/1984 | Bailey | |
| 4,539,996 A | 9/1985 | Engel | |
| 4,569,351 A | 2/1986 | Tang | |
| 4,582,049 A | 4/1986 | Ylvisaker | |
| 4,729,377 A | 3/1988 | Granek et al. | |
| 4,739,764 A | 4/1988 | Lue et al. | |
| 4,763,659 A | 8/1988 | Dunseath, Jr. | |
| 4,771,779 A | 9/1988 | Tanagho et al. | |
| 4,981,146 A | 1/1991 | Bertolucci | |
| 4,982,432 A | 1/1991 | Clark et al. | |

(Continued)

FOREIGN PATENT DOCUMENTS

| | | |
|---|---|---|
| CN | 1135722 | 11/1996 |
| CN | 1547483 | 11/2004 |

(Continued)

OTHER PUBLICATIONS

Apartis; Clinical neurophysiology in movement disorders. Handb Clin Neurol; 111; Pediatric Neurology Pt. 1; pp. 87-92;Apr. 2013.

(Continued)

*Primary Examiner* — Michael W Kahelin

(74) *Attorney, Agent, or Firm* — Knobbe, Martens, Olson & Bear, LLP

(57) ABSTRACT

Systems, devices, and methods for electrically stimulating peripheral nerve(s) to treat various disorders are disclosed, as well as signal processing systems and methods for enhancing diagnostic and therapeutic protocols relating to the same.

19 Claims, 9 Drawing Sheets

(56) References Cited

U.S. PATENT DOCUMENTS

| | | |
|---|---|---|
| 4,996,987 A * | 3/1991 | Petrofsky .......... A61N 1/36003 |
| | | 607/66 |
| 5,003,978 A | 4/1991 | Dunseath, Jr. |
| 5,052,391 A | 10/1991 | Silverstone et al. |
| 5,070,862 A | 12/1991 | Berlant |
| 5,137,507 A | 8/1992 | Park |
| 5,330,516 A | 7/1994 | Nathan |
| 5,397,338 A | 3/1995 | Grey et al. |
| 5,514,175 A | 5/1996 | Kim et al. |
| 5,540,235 A | 7/1996 | Wilson |
| 5,562,707 A | 10/1996 | Prochazka et al. |
| 5,562,717 A | 10/1996 | Tippey et al. |
| 5,573,011 A | 11/1996 | Felsing |
| 5,575,294 A | 11/1996 | Perry et al. |
| 5,606,968 A | 3/1997 | Mang |
| 5,643,173 A | 7/1997 | Welles |
| 5,775,331 A | 7/1998 | Raymond et al. |
| 5,833,709 A | 11/1998 | Rise et al. |
| 5,833,716 A | 11/1998 | Bar-Or et al. |
| 5,899,922 A | 5/1999 | Loos |
| 6,016,449 A | 1/2000 | Fischell et al. |
| 6,076,018 A | 6/2000 | Sturman et al. |
| 6,081,744 A | 6/2000 | Loos |
| 6,161,044 A | 12/2000 | Silverstone |
| 6,178,352 B1 | 1/2001 | Gruzdowich et al. |
| 6,351,674 B2 | 2/2002 | Silverstone |
| 6,366,813 B1 | 4/2002 | DiLorenzo |
| 6,366,814 B1 | 4/2002 | Boveja et al. |
| 6,445,955 B1 | 9/2002 | Michelson et al. |
| 6,449,512 B1 | 9/2002 | Boveja |
| 6,453,204 B1 | 9/2002 | Rhoads |
| 6,505,074 B2 | 1/2003 | Boveja et al. |
| 6,546,290 B1 | 4/2003 | Shloznikov |
| 6,564,103 B2 | 5/2003 | Fischer et al. |
| 6,579,270 B2 | 6/2003 | Sussman et al. |
| 6,652,449 B1 | 11/2003 | Gross et al. |
| 6,678,548 B1 | 1/2004 | Echauz et al. |
| 6,701,185 B2 | 3/2004 | Burnett et al. |
| 6,704,603 B1 | 3/2004 | Gesotti |
| 6,731,987 B1 | 5/2004 | McAdams et al. |
| 6,735,474 B1 | 5/2004 | Loeb et al. |
| 6,735,480 B2 | 5/2004 | Giuntoli et al. |
| 6,788,976 B2 | 9/2004 | Gesotti |
| 6,819,956 B2 | 11/2004 | DiLorenzo |
| 6,829,510 B2 | 12/2004 | Nathan et al. |
| 6,836,684 B1 | 12/2004 | Rijkhoff et al. |
| 6,862,480 B2 | 3/2005 | Cohen et al. |
| 6,892,098 B2 | 5/2005 | Ayal et al. |
| 6,937,905 B2 | 8/2005 | Carroll et al. |
| 6,959,215 B2 | 10/2005 | Gliner et al. |
| 6,959,216 B2 | 10/2005 | Faghri |
| 6,988,005 B2 | 1/2006 | McGraw et al. |
| 7,010,352 B2 | 3/2006 | Hogan |
| 7,089,061 B2 | 8/2006 | Grey |
| 7,146,220 B2 | 12/2006 | Dar et al. |
| 7,162,305 B2 | 1/2007 | Tong et al. |
| 7,171,266 B2 | 1/2007 | Gruzdowich et al. |
| 7,177,694 B2 | 2/2007 | Elbaum |
| 7,177,703 B2 | 2/2007 | Boveja et al. |
| 7,209,787 B2 | 4/2007 | DiLorenzo |
| 7,228,178 B2 | 6/2007 | Carroll et al. |
| 7,231,254 B2 | 6/2007 | DiLorenzo |
| 7,236,830 B2 | 6/2007 | Gliner |
| 7,254,444 B2 | 8/2007 | Moore et al. |
| 7,277,758 B2 | 10/2007 | DiLorenzo |
| 7,324,851 B1 | 1/2008 | DiLorenzo |
| 7,326,235 B2 | 2/2008 | Edwards |
| 7,328,068 B2 | 2/2008 | Spinelli et al. |
| 7,349,739 B2 | 3/2008 | Harry et al. |
| 7,353,064 B2 | 4/2008 | Gliner et al. |
| 7,369,896 B2 | 5/2008 | Gesotti |
| 7,499,747 B2 | 3/2009 | Kieval et al. |
| 7,529,582 B1 | 5/2009 | DiLorenzo |
| 7,558,610 B1 | 7/2009 | Odderson |
| 7,636,602 B2 | 12/2009 | Baru Fassio et al. |
| 7,643,880 B2 | 1/2010 | Tanagho et al. |
| 7,643,882 B2 | 1/2010 | Boston |
| 7,647,112 B2 | 1/2010 | Tracey et al. |
| 7,650,190 B2 | 1/2010 | Zhou et al. |
| 7,657,317 B2 | 2/2010 | Thacker et al. |
| 7,742,820 B2 | 6/2010 | Wyler et al. |
| 7,761,166 B2 | 7/2010 | Giftakis et al. |
| 7,769,464 B2 | 8/2010 | Gerber et al. |
| 7,857,771 B2 | 12/2010 | Alwan et al. |
| 7,899,527 B2 | 3/2011 | Yun et al. |
| 7,899,556 B2 | 3/2011 | Nathan et al. |
| 7,917,201 B2 | 3/2011 | Gozani et al. |
| 7,930,034 B2 | 4/2011 | Gerber |
| 7,949,403 B2 | 5/2011 | Palermo et al. |
| 7,957,814 B2 | 6/2011 | Goetz et al. |
| 7,974,696 B1 | 7/2011 | DiLorenzo |
| 7,974,698 B2 | 7/2011 | Tass et al. |
| 7,991,476 B2 | 8/2011 | Nachum |
| 7,996,088 B2 | 8/2011 | Marrosu et al. |
| 7,998,092 B2 | 8/2011 | Avni et al. |
| 8,000,796 B2 | 8/2011 | Tass et al. |
| 8,025,632 B2 | 9/2011 | Einarsson |
| 8,046,083 B2 | 10/2011 | Teganthoff et al. |
| 8,075,499 B2 | 12/2011 | Nathan et al. |
| 8,086,318 B2 | 12/2011 | Strother et al. |
| 8,121,694 B2 | 2/2012 | Molnar et al. |
| 8,145,316 B2 | 3/2012 | Deem et al. |
| 8,165,668 B2 | 4/2012 | Dacey, Jr. et al. |
| 8,165,685 B1 | 4/2012 | Knutson et al. |
| 8,170,658 B2 | 5/2012 | Dacey, Jr. et al. |
| 8,175,718 B2 | 5/2012 | Wahlgren et al. |
| 8,187,209 B1 | 5/2012 | Guiffrida et al. |
| 8,190,249 B1 | 5/2012 | Gharieb et al. |
| 8,195,287 B2 | 6/2012 | Dacey, Jr. et al. |
| 8,209,036 B2 | 6/2012 | Nathan et al. |
| 8,219,188 B2 | 7/2012 | Craig |
| 8,233,988 B2 | 7/2012 | Errico et al. |
| 8,260,439 B2 | 9/2012 | Diubaldi et al. |
| 8,265,763 B2 | 9/2012 | Fahey |
| 8,301,215 B2 | 10/2012 | Lee |
| 8,306,624 B2 | 11/2012 | Gerber et al. |
| 8,308,665 B2 | 11/2012 | Harry et al. |
| 8,313,443 B2 | 11/2012 | Tom |
| 8,326,432 B2 | 12/2012 | Kalisek |
| 8,343,026 B2 | 1/2013 | Gardiner et al. |
| 8,364,257 B2 | 1/2013 | Van Den Eerenbeemd et al. |
| 8,374,701 B2 | 2/2013 | Hyde et al. |
| 8,380,314 B2 | 2/2013 | Panken et al. |
| 8,382,688 B2 | 2/2013 | Dar et al. |
| 8,391,970 B2 | 3/2013 | Tracey et al. |
| 8,396,556 B2 | 3/2013 | Libbus et al. |
| 8,406,841 B2 | 3/2013 | Lin et al. |
| 8,409,116 B2 | 4/2013 | Wang et al. |
| 8,412,338 B2 | 4/2013 | Faltys |
| 8,414,507 B2 | 4/2013 | Asada |
| 8,417,351 B2 | 4/2013 | Kilger |
| 8,428,719 B2 | 4/2013 | Napadow |
| 8,430,805 B2 | 4/2013 | Burnett et al. |
| 8,435,166 B2 | 5/2013 | Burnett et al. |
| 8,447,411 B2 | 5/2013 | Skelton et al. |
| 8,452,410 B2 | 5/2013 | Emborg et al. |
| 8,463,374 B2 | 6/2013 | Hudson et al. |
| 8,473,064 B2 | 6/2013 | Castel et al. |
| 8,548,594 B2 | 10/2013 | Thimineur et al. |
| 8,571,687 B2 | 10/2013 | Libbus et al. |
| 8,581,731 B2 | 11/2013 | Purks et al. |
| 8,583,238 B1 | 11/2013 | Heldman et al. |
| 8,588,884 B2 | 11/2013 | Hegde et al. |
| 8,588,917 B2 | 11/2013 | Whitehurst et al. |
| 8,608,671 B2 | 12/2013 | Kinoshita et al. |
| 8,626,305 B2 | 1/2014 | Nielsen et al. |
| 8,639,342 B2 | 1/2014 | Possover |
| 8,644,904 B2 | 2/2014 | Chang et al. |
| 8,644,938 B2 | 2/2014 | Craggs |
| 8,660,656 B2 | 2/2014 | Moser et al. |
| 8,666,496 B2 | 3/2014 | Simon et al. |
| 8,679,038 B1 | 3/2014 | Giuffrida |
| 8,682,441 B2 | 3/2014 | De Ridder |
| 8,688,220 B2 | 4/2014 | Degiorgio et al. |

(56) References Cited

U.S. PATENT DOCUMENTS

| | | |
|---|---|---|
| 8,694,104 B2 | 4/2014 | Libbus et al. |
| 8,694,110 B2 | 4/2014 | Nathan et al. |
| 8,702,584 B2 | 4/2014 | Rigaux et al. |
| 8,702,629 B2 | 4/2014 | Giuffrida et al. |
| 8,706,241 B2 | 4/2014 | Firlik et al. |
| 8,718,780 B2 | 5/2014 | Lee |
| 8,738,143 B2 | 5/2014 | Tucker et al. |
| 8,740,825 B2 | 6/2014 | Ehrenreich et al. |
| 8,744,587 B2 | 6/2014 | Miesel et al. |
| 8,755,892 B2 | 6/2014 | Amurthur et al. |
| 8,768,452 B2 | 7/2014 | Gerber |
| 8,788,045 B2 | 7/2014 | Gross et al. |
| 8,788,049 B2 | 7/2014 | Lasko et al. |
| 8,792,977 B2 | 7/2014 | Kakei et al. |
| 8,798,698 B2 | 8/2014 | Kim et al. |
| 8,821,416 B2 | 9/2014 | Johansson et al. |
| 8,825,163 B2 | 9/2014 | Grill et al. |
| 8,825,165 B2 | 9/2014 | Possover |
| 8,843,201 B1 | 9/2014 | Heldman et al. |
| 8,845,494 B2 | 9/2014 | Whitall et al. |
| 8,845,557 B1 | 9/2014 | Giuffrida et al. |
| 8,855,775 B2 | 10/2014 | Leyde |
| 8,862,238 B2 | 10/2014 | Rahimi et al. |
| 8,862,247 B2 | 10/2014 | Schoendorf et al. |
| 8,868,177 B2 | 10/2014 | Simon et al. |
| 8,874,227 B2 | 10/2014 | Simon et al. |
| 8,880,175 B2 | 11/2014 | Simon |
| 8,886,321 B2 | 11/2014 | Rohrer et al. |
| 8,892,200 B2 | 11/2014 | Wagner et al. |
| 8,897,870 B2 | 11/2014 | De Ridder |
| 8,903,494 B2 | 12/2014 | Goldwasser et al. |
| 8,920,345 B2 | 12/2014 | Greenberg et al. |
| 8,923,970 B2 | 12/2014 | Bar-Yoseph et al. |
| 8,948,876 B2 | 2/2015 | Gozani et al. |
| 8,961,439 B2 | 2/2015 | Yang et al. |
| 8,972,017 B2 | 3/2015 | Dar et al. |
| 8,989,861 B2 | 3/2015 | Su et al. |
| 9,002,477 B2 | 4/2015 | Burnett |
| 9,005,102 B2 | 4/2015 | Burnett et al. |
| 9,008,781 B2 | 4/2015 | Ahmed |
| 9,011,310 B2 | 4/2015 | Ahmed |
| 9,017,273 B2 | 4/2015 | Burbank et al. |
| 9,026,216 B2 | 5/2015 | Rossi et al. |
| 9,042,988 B2 | 5/2015 | Dilorenzo |
| 9,060,747 B2 | 6/2015 | Salorio |
| 9,089,691 B2 | 7/2015 | Libbus et al. |
| 9,095,351 B2 | 8/2015 | Sachs et al. |
| 9,095,417 B2 | 8/2015 | Dar et al. |
| 9,107,614 B2 | 8/2015 | Halkias et al. |
| 9,119,964 B2 | 9/2015 | Marnfeldt |
| 9,155,885 B2 | 10/2015 | Wei et al. |
| 9,155,890 B2 | 10/2015 | Guntinas-Lichius et al. |
| 9,162,059 B1 | 10/2015 | Lindenthaler |
| 9,168,374 B2 | 10/2015 | Su |
| 9,174,045 B2 | 11/2015 | Simon et al. |
| 9,186,095 B2 | 11/2015 | Machado et al. |
| 9,192,763 B2 | 11/2015 | Gerber et al. |
| 9,220,431 B2 | 12/2015 | Holzhacker |
| 9,220,895 B2 | 12/2015 | Siff et al. |
| 9,227,056 B1 | 1/2016 | Heldman et al. |
| 9,238,137 B2 | 1/2016 | Einav et al. |
| 9,238,142 B2 | 1/2016 | Heldman et al. |
| 9,242,085 B2 | 1/2016 | Hershey et al. |
| 9,248,285 B2 | 2/2016 | Haessler |
| 9,248,286 B2 | 2/2016 | Simon et al. |
| 9,248,297 B2 | 2/2016 | Hoyer et al. |
| 9,254,382 B2 | 2/2016 | Ahmad et al. |
| 9,259,577 B2 | 2/2016 | Kaula et al. |
| 9,265,927 B2 | 2/2016 | Yonce et al. |
| 9,282,928 B1 | 3/2016 | Giffrida |
| 9,289,607 B2 | 3/2016 | Su et al. |
| 9,301,712 B2 | 4/2016 | McNames et al. |
| 9,302,046 B1 | 4/2016 | Giuffrida et al. |
| 9,311,686 B2 | 4/2016 | Roush et al. |
| 9,314,190 B1 | 4/2016 | Giuffrida et al. |
| 9,314,622 B2 | 4/2016 | Embrey et al. |
| 9,332,918 B1 | 5/2016 | Buckley et al. |
| 9,339,213 B2 | 5/2016 | Otsamo et al. |
| 9,339,641 B2 | 5/2016 | Rajguru et al. |
| 9,345,872 B2 | 5/2016 | Groteke |
| 9,364,657 B2 | 6/2016 | Kiani et al. |
| 9,364,672 B2 | 6/2016 | Marnfeldt |
| 9,375,570 B2 | 6/2016 | Kiani et al. |
| 9,387,338 B2 | 7/2016 | Burnett |
| 9,393,430 B2 | 7/2016 | Demers et al. |
| 9,408,683 B2 | 8/2016 | St. Anne et al. |
| 9,414,776 B2 | 8/2016 | Sillay et al. |
| 9,415,205 B2 | 8/2016 | Lasko et al. |
| 9,452,287 B2 | 9/2016 | Rosenbluth et al. |
| 9,468,753 B2 | 10/2016 | Fisher et al. |
| 9,474,898 B2 | 10/2016 | Gozani et al. |
| 9,549,872 B2 | 1/2017 | Chen et al. |
| 9,581,972 B1 | 2/2017 | Arrow et al. |
| 9,586,038 B1 | 3/2017 | Kosierkiewicz |
| 9,589,698 B2 | 3/2017 | Anhalt et al. |
| 9,597,509 B2 | 3/2017 | Hoffer et al. |
| 9,610,442 B2 | 4/2017 | Yoo et al. |
| 9,610,459 B2 | 4/2017 | Burnett et al. |
| 9,615,797 B2 | 4/2017 | John |
| 9,630,004 B2 | 4/2017 | Rajguru et al. |
| 9,649,486 B2 | 5/2017 | Holzhacker |
| 9,656,070 B2 | 5/2017 | Gozani et al. |
| 9,669,211 B2 | 6/2017 | Wijting et al. |
| 9,675,800 B2 | 6/2017 | Li et al. |
| 9,675,801 B2 | 6/2017 | Kong et al. |
| 9,707,393 B2 | 7/2017 | Hsueh et al. |
| 9,731,126 B2 | 8/2017 | Ferree et al. |
| 9,757,584 B2 | 9/2017 | Burnett |
| 9,782,584 B2 | 10/2017 | Cartledge et al. |
| 9,802,041 B2 | 10/2017 | Wong et al. |
| 9,861,283 B1 | 1/2018 | Giuffrida |
| 9,877,679 B1 | 1/2018 | Giuffrida |
| 9,877,680 B1 | 1/2018 | Giuffrida et al. |
| 9,884,179 B2 | 2/2018 | Bouton et al. |
| 9,924,899 B2 | 3/2018 | Pracar et al. |
| 9,956,395 B2 | 5/2018 | Bikson et al. |
| 9,974,478 B1 | 5/2018 | Brokaw et al. |
| 9,980,659 B2 | 5/2018 | Sadeghian-Motahar et al. |
| 9,992,918 B2 | 6/2018 | Watanabe et al. |
| 10,004,900 B2 | 6/2018 | Kent et al. |
| 10,016,600 B2 | 7/2018 | Creasey et al. |
| 10,022,545 B1 | 7/2018 | Giuffrida |
| 10,028,695 B2 | 7/2018 | Machado et al. |
| 10,045,740 B2 | 8/2018 | John |
| 10,046,161 B2 | 8/2018 | Biasiucci et al. |
| 10,076,656 B2 | 9/2018 | Dar et al. |
| 10,080,885 B2 | 9/2018 | Nathan et al. |
| 10,112,040 B2 | 10/2018 | Herb et al. |
| 10,118,035 B2 | 11/2018 | Perez et al. |
| 10,130,809 B2 | 11/2018 | Cartledge et al. |
| 10,130,810 B2 | 11/2018 | Ferree et al. |
| 10,137,025 B2 | 11/2018 | Fior et al. |
| 10,173,060 B2 | 1/2019 | Wong et al. |
| 10,179,238 B2 | 1/2019 | Wong et al. |
| 10,213,593 B2 | 2/2019 | Kaplan et al. |
| 10,213,602 B2 | 2/2019 | Ironi et al. |
| 10,232,174 B2 | 3/2019 | Simon et al. |
| 10,252,053 B2 | 4/2019 | Page et al. |
| 10,285,646 B1 * | 5/2019 | Grant ............... A61B 5/7221 |
| 10,286,210 B2 | 5/2019 | Yoo |
| 10,293,159 B2 | 5/2019 | Kong et al. |
| 10,335,594 B2 | 7/2019 | Lin et al. |
| 10,335,595 B2 | 7/2019 | Ferree et al. |
| 10,342,977 B2 | 7/2019 | Raghunathan |
| 10,398,896 B2 | 9/2019 | Lin et al. |
| 10,456,573 B1 | 10/2019 | Feinstein et al. |
| 10,463,854 B2 | 11/2019 | Perez |
| 10,500,396 B2 | 12/2019 | Tamaki et al. |
| 10,537,732 B2 | 1/2020 | Nachum et al. |
| 10,549,093 B2 | 2/2020 | Wong et al. |
| 10,556,107 B2 | 2/2020 | Yoo et al. |
| 10,561,839 B2 | 2/2020 | Wong et al. |
| 10,603,482 B2 | 3/2020 | Hamner et al. |
| 10,610,114 B2 | 4/2020 | Buckley et al. |

(56) References Cited

U.S. PATENT DOCUMENTS

| | | |
|---|---|---|
| 10,625,074 B2 | 4/2020 | Rosenbluth et al. |
| 10,632,312 B2 | 4/2020 | Ziv |
| 10,661,082 B2 | 5/2020 | Kerselaers |
| 10,722,709 B2 | 7/2020 | Yoo et al. |
| 10,765,856 B2 | 9/2020 | Wong et al. |
| 10,773,079 B2 | 9/2020 | Keller et al. |
| 10,780,269 B2 | 9/2020 | Gozani et al. |
| 10,786,669 B2 | 9/2020 | Rajguru et al. |
| 10,814,130 B2 | 10/2020 | Wong et al. |
| 10,814,131 B2 | 10/2020 | Goldwasser et al. |
| 10,835,736 B2 | 11/2020 | Horter et al. |
| 10,850,090 B2 | 12/2020 | Rosenbluth et al. |
| 10,870,002 B2 | 12/2020 | Wybo et al. |
| 10,905,879 B2 | 2/2021 | Wong et al. |
| 10,918,853 B2 | 2/2021 | Creasey et al. |
| 10,940,311 B2 | 3/2021 | Gozani et al. |
| 10,945,879 B2 | 3/2021 | Black et al. |
| 10,960,207 B2 | 3/2021 | Wong et al. |
| 10,967,177 B2 | 4/2021 | Lee |
| 11,026,835 B2 | 6/2021 | Black et al. |
| 11,033,206 B2 | 6/2021 | Roh |
| 11,033,731 B2 | 6/2021 | Jeffery et al. |
| 11,033,736 B2 | 6/2021 | Edgerton et al. |
| 11,058,867 B2 | 7/2021 | Nathan et al. |
| 11,077,300 B2 | 8/2021 | McBride |
| 11,077,301 B2 | 8/2021 | Creasey et al. |
| 11,103,699 B1 | 8/2021 | Oppenheim et al. |
| 11,141,586 B2 | 10/2021 | Campean et al. |
| 11,141,587 B2 | 10/2021 | Campean et al. |
| 11,160,971 B2 | 11/2021 | Sharma et al. |
| 11,213,681 B2 | 1/2022 | Raghunathan |
| 11,224,742 B2 | 1/2022 | Burnett |
| 11,247,040 B2 | 2/2022 | Ferree et al. |
| 11,247,053 B2 | 2/2022 | Rajguru et al. |
| 11,266,836 B2 | 3/2022 | Charlesworth et al. |
| 11,318,307 B2 | 5/2022 | Kern et al. |
| 11,331,480 B2 | 5/2022 | Hamner et al. |
| 11,338,120 B2 | 5/2022 | Yun et al. |
| 11,338,128 B2 | 5/2022 | Lawson et al. |
| 11,344,722 B2 | 5/2022 | Wong et al. |
| 11,357,981 B2 | 6/2022 | Moaddeb et al. |
| 11,389,651 B2 | 7/2022 | Tamaki et al. |
| 11,420,052 B2 | 8/2022 | Doskocil et al. |
| 11,484,710 B2 | 11/2022 | Mantovani et al. |
| 11,504,530 B2 | 11/2022 | Herr et al. |
| 11,517,753 B2 | 12/2022 | Rhodes |
| 11,534,605 B2 | 12/2022 | Bouton et al. |
| 11,590,348 B2 | 2/2023 | Moaddeb et al. |
| 11,596,784 B1 | 3/2023 | Hamner et al. |
| 11,596,791 B2 | 3/2023 | Wong et al. |
| 11,596,792 B2 | 3/2023 | Campean et al. |
| 11,628,300 B2 | 4/2023 | Rajguru et al. |
| 11,642,513 B2 | 5/2023 | Sharma et al. |
| 11,672,981 B2 | 6/2023 | Jaasma et al. |
| 11,766,191 B2 | 9/2023 | Sharma et al. |
| 11,833,352 B2 | 12/2023 | Law et al. |
| 11,839,762 B2 | 12/2023 | Doskocil et al. |
| 11,844,943 B2 | 12/2023 | Rajguru et al. |
| 11,857,778 B2 | 1/2024 | Hamner et al. |
| 11,872,399 B2 | 1/2024 | Raghunathan |
| 11,878,166 B2 | 1/2024 | Colburn et al. |
| 11,890,468 B1 | 2/2024 | Yu |
| 11,890,469 B2 | 2/2024 | Moaddeb et al. |
| 11,896,824 B2 | 2/2024 | Doskocil |
| 11,911,604 B2 | 2/2024 | Sharma et al. |
| 11,918,806 B2 | 3/2024 | Wong et al. |
| 11,975,190 B2 | 5/2024 | Cho et al. |
| 11,992,685 B2 | 5/2024 | Kassiri Bidhendi et al. |
| 2001/0020177 A1 | 9/2001 | Gruzdowich et al. |
| 2002/0055761 A1 | 5/2002 | Mann et al. |
| 2002/0161415 A1 | 10/2002 | Cohen et al. |
| 2002/0165586 A1 | 11/2002 | Hill et al. |
| 2002/0177882 A1 | 11/2002 | DiLorenzo |
| 2003/0032992 A1 | 2/2003 | Thacker et al. |
| 2003/0045922 A1 | 3/2003 | Northrop |
| 2003/0088294 A1 | 5/2003 | Gesotti |
| 2003/0093098 A1 | 5/2003 | Heitzmann et al. |
| 2003/0149457 A1 | 8/2003 | Tcheng et al. |
| 2003/0181959 A1 | 9/2003 | Dobak, III |
| 2003/0187483 A1 | 10/2003 | Grey et al. |
| 2003/0195583 A1 | 10/2003 | Gruzdowich et al. |
| 2004/0015094 A1 | 1/2004 | Manabe et al. |
| 2004/0088025 A1 | 5/2004 | Gessotti |
| 2004/0093093 A1 | 5/2004 | Andrews |
| 2004/0102819 A1 | 5/2004 | Zou et al. |
| 2004/0127939 A1 | 7/2004 | Grey et al. |
| 2004/0133249 A1 | 7/2004 | Gesotti |
| 2004/0167588 A1 | 8/2004 | Bertolucci |
| 2004/0249416 A1 | 12/2004 | Yun et al. |
| 2004/0267331 A1 | 12/2004 | Koeneman et al. |
| 2005/0021103 A1 | 1/2005 | DiLorenzo |
| 2005/0055063 A1 | 3/2005 | Loeb et al. |
| 2005/0060009 A1 | 3/2005 | Geotz |
| 2005/0065553 A1 | 3/2005 | Ben Ezra et al. |
| 2005/0075502 A1 | 4/2005 | Shafer |
| 2005/0171576 A1 | 8/2005 | Williams et al. |
| 2005/0171577 A1 | 8/2005 | Cohen et al. |
| 2005/0182454 A1 | 8/2005 | Gharib et al. |
| 2005/0222626 A1 | 10/2005 | DiLorenzo |
| 2005/0234309 A1 | 10/2005 | Klapper |
| 2005/0240241 A1 | 10/2005 | Yun et al. |
| 2006/0015153 A1 | 1/2006 | Gliner et al. |
| 2006/0047326 A1 | 3/2006 | Wheeler |
| 2006/0052726 A1 | 3/2006 | Weisz et al. |
| 2006/0074450 A1 | 4/2006 | Boveja et al. |
| 2006/0095088 A1 | 5/2006 | De Ridder |
| 2006/0161218 A1 | 7/2006 | Danilov |
| 2006/0173509 A1 | 8/2006 | Lee et al. |
| 2006/0184059 A1 | 8/2006 | Jadidi |
| 2006/0217781 A1 | 9/2006 | John |
| 2006/0224191 A1 | 10/2006 | DiLorenzo |
| 2006/0229678 A1 | 10/2006 | Lee |
| 2006/0253167 A1 | 11/2006 | Kurtz et al. |
| 2006/0276853 A1 | 12/2006 | Tass |
| 2006/0293723 A1 | 12/2006 | Whitehurst et al. |
| 2007/0027486 A1 | 2/2007 | Armstrong |
| 2007/0073361 A1 | 3/2007 | Goren et al. |
| 2007/0123951 A1 | 5/2007 | Boston |
| 2007/0123952 A1 | 5/2007 | Strother et al. |
| 2007/0142862 A1 | 6/2007 | DiLorenzo |
| 2007/0156179 A1 | 7/2007 | Karashurov |
| 2007/0156182 A1 | 7/2007 | Castel et al. |
| 2007/0156183 A1 | 7/2007 | Rhodes |
| 2007/0156200 A1 | 7/2007 | Kornet et al. |
| 2007/0173899 A1 | 7/2007 | Levin et al. |
| 2007/0173903 A1 | 7/2007 | Goren et al. |
| 2007/0203533 A1 | 8/2007 | Goren et al. |
| 2007/0203534 A1 | 8/2007 | Tapper |
| 2007/0207193 A1 | 9/2007 | Zasler et al. |
| 2007/0249952 A1 | 10/2007 | Rubin et al. |
| 2007/0255319 A1* | 11/2007 | Greenberg ........... A61N 1/0543 607/2 |
| 2007/0276217 A1 | 11/2007 | Brown et al. |
| 2007/0282228 A1 | 12/2007 | Einav et al. |
| 2008/0004672 A1 | 1/2008 | Dalal et al. |
| 2008/0009772 A1 | 1/2008 | Tyler et al. |
| 2008/0021505 A1 | 1/2008 | Hastings et al. |
| 2008/0027507 A1 | 1/2008 | Bijelic et al. |
| 2008/0030170 A1 | 2/2008 | Dacuay et al. |
| 2008/0033259 A1 | 2/2008 | Manto et al. |
| 2008/0033504 A1 | 2/2008 | Bertolucci |
| 2008/0051839 A1 | 2/2008 | Libbus et al. |
| 2008/0051845 A1* | 2/2008 | Mentelos ............. A61B 5/6843 607/28 |
| 2008/0058773 A1 | 3/2008 | John |
| 2008/0058871 A1 | 3/2008 | Libbus et al. |
| 2008/0058893 A1 | 3/2008 | Noujokat |
| 2008/0097564 A1 | 4/2008 | Lathrop |
| 2008/0147146 A1 | 6/2008 | Wahlgren et al. |
| 2008/0177398 A1 | 7/2008 | Gross et al. |
| 2008/0195007 A1 | 8/2008 | Podrazhansky et al. |
| 2008/0208282 A1 | 8/2008 | Gelfand et al. |
| 2008/0208288 A1 | 8/2008 | Podrazhansky et al. |
| 2008/0216593 A1 | 9/2008 | Jacobsen et al. |

(56) References Cited

U.S. PATENT DOCUMENTS

| | | |
|---|---|---|
| 2008/0243204 A1 | 10/2008 | Uthman et al. |
| 2008/0288016 A1 | 11/2008 | Amurthur et al. |
| 2008/0300449 A1 | 12/2008 | Gerber et al. |
| 2008/0306325 A1 | 12/2008 | Burnett et al. |
| 2008/0312520 A1 | 12/2008 | Rowlandson et al. |
| 2009/0018609 A1 | 1/2009 | DiLorenzo |
| 2009/0076565 A1 | 3/2009 | Surwit |
| 2009/0082831 A1 | 3/2009 | Paul et al. |
| 2009/0099623 A1 | 4/2009 | Bentwich |
| 2009/0105785 A1 | 4/2009 | Wei et al. |
| 2009/0112133 A1 | 4/2009 | Deisseroth et al. |
| 2009/0157138 A1 | 6/2009 | Errico et al. |
| 2009/0187121 A1 | 7/2009 | Evans |
| 2009/0216294 A1 | 8/2009 | Ewing et al. |
| 2009/0222053 A1 | 9/2009 | Gaunt et al. |
| 2009/0247910 A1 | 10/2009 | Klapper |
| 2009/0249617 A1 | 10/2009 | Karicherla et al. |
| 2009/0299435 A1 | 12/2009 | Gliner et al. |
| 2009/0312690 A1 | 12/2009 | Kim et al. |
| 2009/0318986 A1 | 12/2009 | Alo et al. |
| 2009/0326595 A1 | 12/2009 | Brockway et al. |
| 2009/0326607 A1 | 12/2009 | Castel et al. |
| 2010/0004715 A1 | 1/2010 | Fahey |
| 2010/0010381 A1 | 1/2010 | Skelton et al. |
| 2010/0010383 A1 | 1/2010 | Skelton et al. |
| 2010/0010572 A1 | 1/2010 | Skelton et al. |
| 2010/0057154 A1 | 3/2010 | Dietrich et al. |
| 2010/0059722 A1 | 3/2010 | Copp-Howland et al. |
| 2010/0076533 A1 | 3/2010 | Dar et al. |
| 2010/0099963 A1 | 4/2010 | Kilger |
| 2010/0107657 A1 | 5/2010 | Vistakula |
| 2010/0125220 A1 | 5/2010 | Seong |
| 2010/0152817 A1 | 6/2010 | Gillbe |
| 2010/0168501 A1 | 7/2010 | Burnett et al. |
| 2010/0168604 A1 | 7/2010 | Echauz |
| 2010/0174342 A1 | 7/2010 | Boston et al. |
| 2010/0222630 A1 | 9/2010 | Mangrum et al. |
| 2010/0227330 A1 | 9/2010 | Fink et al. |
| 2010/0228180 A1 | 9/2010 | Jayes et al. |
| 2010/0249637 A1 | 9/2010 | Walter et al. |
| 2010/0292527 A1 | 11/2010 | Schneider et al. |
| 2010/0298905 A1 | 11/2010 | Simon |
| 2010/0324611 A1 | 12/2010 | Deming et al. |
| 2011/0004268 A1 | 1/2011 | Tcheng et al. |
| 2011/0009920 A1 | 1/2011 | Whitehurst et al. |
| 2011/0021899 A1 | 1/2011 | Arps et al. |
| 2011/0040204 A1 | 2/2011 | Ivorra et al. |
| 2011/0040288 A1 | 2/2011 | Eckstein et al. |
| 2011/0054358 A1 | 3/2011 | Kim et al. |
| 2011/0071590 A1 | 3/2011 | Mounaim et al. |
| 2011/0098780 A1 | 4/2011 | Graupe et al. |
| 2011/0112605 A1 | 5/2011 | Fahey |
| 2011/0118805 A1 | 5/2011 | Wei et al. |
| 2011/0125212 A1 | 5/2011 | Tyler |
| 2011/0137375 A1 | 6/2011 | McBride |
| 2011/0184489 A1 | 7/2011 | Nicolelis et al. |
| 2011/0196446 A1 | 8/2011 | Wu |
| 2011/0202107 A1 | 8/2011 | Sunagawa et al. |
| 2011/0208444 A1 | 8/2011 | Solinky |
| 2011/0213278 A1 | 9/2011 | Horak et al. |
| 2011/0224571 A1 | 9/2011 | Pascual-Leone et al. |
| 2011/0230701 A1 | 9/2011 | Simon et al. |
| 2011/0245734 A1 | 10/2011 | Wagner et al. |
| 2011/0250297 A1 | 10/2011 | Oronsky et al. |
| 2011/0282412 A1 | 11/2011 | Glukhovsky et al. |
| 2011/0288615 A1 | 11/2011 | Armstrong et al. |
| 2011/0301663 A1 | 12/2011 | Wang et al. |
| 2012/0010492 A1 | 1/2012 | Thramann et al. |
| 2012/0046535 A1 | 2/2012 | Lin et al. |
| 2012/0050298 A1 | 3/2012 | Hoffman |
| 2012/0053491 A1 | 3/2012 | Nathan et al. |
| 2012/0059298 A1 | 3/2012 | Hoffman et al. |
| 2012/0078319 A1 | 3/2012 | De Ridder |
| 2012/0088986 A1 | 4/2012 | David et al. |
| 2012/0092178 A1 | 4/2012 | Callsen et al. |
| 2012/0098493 A1 | 4/2012 | Budike |
| 2012/0101326 A1 | 4/2012 | Simon et al. |
| 2012/0109013 A1 | 5/2012 | Everett et al. |
| 2012/0136410 A1 | 5/2012 | Rezai et al. |
| 2012/0158094 A1 | 6/2012 | Kramer et al. |
| 2012/0184801 A1 | 7/2012 | Simon et al. |
| 2012/0185020 A1 | 7/2012 | Simon et al. |
| 2012/0211013 A1 | 8/2012 | Otis |
| 2012/0220812 A1 | 8/2012 | Mishelevich |
| 2012/0239112 A1 | 9/2012 | Muraoka |
| 2012/0245483 A1 | 9/2012 | Lundqvist |
| 2012/0259255 A1 | 10/2012 | Tomlinson et al. |
| 2012/0277621 A1 | 11/2012 | Gerber et al. |
| 2012/0289869 A1 | 11/2012 | Tyler |
| 2012/0290036 A1 | 11/2012 | Karamanoglu et al. |
| 2012/0302821 A1 | 11/2012 | Burnett |
| 2012/0310298 A1 | 12/2012 | Besio et al. |
| 2012/0310299 A1 | 12/2012 | Norbert et al. |
| 2012/0310303 A1 | 12/2012 | Popovic et al. |
| 2012/0330182 A1 | 12/2012 | Alberts et al. |
| 2013/0006322 A1 | 1/2013 | Tai |
| 2013/0035745 A1 | 2/2013 | Ahmed et al. |
| 2013/0053817 A1 | 2/2013 | Yun et al. |
| 2013/0060124 A1 | 3/2013 | Zietsma |
| 2013/0066388 A1 | 3/2013 | Bernhard et al. |
| 2013/0066395 A1 | 3/2013 | Simon et al. |
| 2013/0085317 A1 | 4/2013 | Feinstein |
| 2013/0090519 A1 | 4/2013 | Tass |
| 2013/0106684 A1 | 5/2013 | Weast et al. |
| 2013/0116606 A1 | 5/2013 | Cordo |
| 2013/0123568 A1 | 5/2013 | Hamilton et al. |
| 2013/0123666 A1 | 5/2013 | Giuffrida et al. |
| 2013/0131484 A1 | 5/2013 | Pernu |
| 2013/0131770 A1 | 5/2013 | Rezai |
| 2013/0158624 A1 | 6/2013 | Bain et al. |
| 2013/0158627 A1 | 6/2013 | Gozani et al. |
| 2013/0178765 A1 | 7/2013 | Mishelevich |
| 2013/0211471 A1 | 8/2013 | Libbus et al. |
| 2013/0231713 A1 | 9/2013 | De Ridder et al. |
| 2013/0236867 A1 | 9/2013 | Avni et al. |
| 2013/0238049 A1 | 9/2013 | Simon et al. |
| 2013/0245486 A1 | 9/2013 | Simon et al. |
| 2013/0245713 A1 | 9/2013 | Tass |
| 2013/0253299 A1 | 9/2013 | Weber et al. |
| 2013/0267759 A1 | 10/2013 | Jin |
| 2013/0281890 A1 | 10/2013 | Mishelevich |
| 2013/0289647 A1 | 10/2013 | Bhadra et al. |
| 2013/0296967 A1 | 11/2013 | Skaribas et al. |
| 2013/0297022 A1 | 11/2013 | Pathak |
| 2013/0331907 A1 | 12/2013 | Sumners et al. |
| 2013/0333094 A1 | 12/2013 | Rogers et al. |
| 2013/0338726 A1 | 12/2013 | Machado |
| 2014/0025059 A1 | 1/2014 | Kerr |
| 2014/0031605 A1 | 1/2014 | Schneider |
| 2014/0039573 A1 | 2/2014 | Jindra |
| 2014/0039575 A1 | 2/2014 | Bradley |
| 2014/0046423 A1 | 2/2014 | Rajguru et al. |
| 2014/0058189 A1 | 2/2014 | Stubbeman |
| 2014/0067003 A1 | 3/2014 | Vase et al. |
| 2014/0078694 A1 | 3/2014 | Wissmar |
| 2014/0081345 A1 | 3/2014 | Hershey |
| 2014/0094675 A1 | 4/2014 | Luna et al. |
| 2014/0094873 A1 | 4/2014 | Emborg et al. |
| 2014/0128939 A1 | 5/2014 | Embrey et al. |
| 2014/0132410 A1 | 5/2014 | Chang |
| 2014/0142654 A1 | 5/2014 | Simon et al. |
| 2014/0148872 A1 | 5/2014 | Goldwasser et al. |
| 2014/0148873 A1 | 5/2014 | Kirn |
| 2014/0163444 A1 | 6/2014 | Ingvarsson |
| 2014/0171834 A1 | 6/2014 | DeGoede et al. |
| 2014/0200573 A1 | 7/2014 | Deem et al. |
| 2014/0214119 A1 | 7/2014 | Greiner et al. |
| 2014/0228927 A1 | 8/2014 | Ahmad et al. |
| 2014/0236258 A1 | 8/2014 | Carroll et al. |
| 2014/0246628 A1 | 9/2014 | Anhalt et al. |
| 2014/0249452 A1 | 9/2014 | Marsh et al. |
| 2014/0257047 A1 | 9/2014 | Slliay et al. |
| 2014/0257129 A1 | 9/2014 | Choi et al. |
| 2014/0276194 A1 | 9/2014 | Osorio |

(56) References Cited

U.S. PATENT DOCUMENTS

| | | |
|---|---|---|
| 2014/0277220 A1 | 9/2014 | Brennan et al. |
| 2014/0296752 A1 | 10/2014 | Edgerton et al. |
| 2014/0296934 A1 | 10/2014 | Gozani et al. |
| 2014/0296935 A1* | 10/2014 | Ferree .................. A61N 1/3603 607/46 |
| 2014/0300490 A1 | 10/2014 | Kotz et al. |
| 2014/0309709 A1 | 10/2014 | Gozanl et al. |
| 2014/0316484 A1 | 10/2014 | Edgerton et al. |
| 2014/0324118 A1 | 10/2014 | Simon et al. |
| 2014/0330068 A1 | 11/2014 | Partsch et al. |
| 2014/0330335 A1 | 11/2014 | Errico et al. |
| 2014/0336003 A1 | 11/2014 | Franz et al. |
| 2014/0336722 A1 | 11/2014 | Rocon De Lima et al. |
| 2014/0343462 A1 | 11/2014 | Burnet |
| 2014/0350436 A1 | 11/2014 | Nathan et al. |
| 2014/0358040 A1 | 12/2014 | Kim et al. |
| 2014/0364678 A1 | 12/2014 | Harry et al. |
| 2015/0004656 A1 | 1/2015 | Tang et al. |
| 2015/0005852 A1 | 1/2015 | Hershey et al. |
| 2015/0012067 A1 | 1/2015 | Bradley et al. |
| 2015/0038886 A1 | 2/2015 | Snow |
| 2015/0042315 A1* | 2/2015 | Cen .................. A61B 5/369 600/509 |
| 2015/0044656 A1 | 2/2015 | Eichhorn et al. |
| 2015/0057506 A1 | 2/2015 | Luna et al. |
| 2015/0073310 A1 | 3/2015 | Pracar et al. |
| 2015/0080979 A1 | 3/2015 | Lasko et al. |
| 2015/0100004 A1 | 4/2015 | Goldman et al. |
| 2015/0100104 A1 | 4/2015 | Kiani et al. |
| 2015/0100105 A1 | 4/2015 | Kiani et al. |
| 2015/0148866 A1 | 5/2015 | Bulsen et al. |
| 2015/0148878 A1 | 5/2015 | Yoo et al. |
| 2015/0157274 A1 | 6/2015 | Ghassemzadeh et al. |
| 2015/0164377 A1 | 6/2015 | Nathan et al. |
| 2015/0164401 A1 | 6/2015 | Toth et al. |
| 2015/0190085 A1 | 7/2015 | Nathan et al. |
| 2015/0190634 A1 | 7/2015 | Rezai et al. |
| 2015/0196767 A1 | 7/2015 | Zaghloul |
| 2015/0202444 A1 | 7/2015 | Franke et al. |
| 2015/0208955 A1 | 7/2015 | Smith |
| 2015/0216475 A1 | 8/2015 | Luna et al. |
| 2015/0230733 A1 | 8/2015 | Heo et al. |
| 2015/0230756 A1 | 8/2015 | Luna et al. |
| 2015/0277559 A1 | 10/2015 | Vescovi et al. |
| 2015/0297901 A1 | 10/2015 | Kockx |
| 2015/0321000 A1 | 11/2015 | Rosenbluth et al. |
| 2015/0335882 A1 | 11/2015 | Gross et al. |
| 2016/0001096 A1 | 1/2016 | Mishelevich |
| 2016/0008620 A1 | 1/2016 | Stubbeman |
| 2016/0016014 A1 | 1/2016 | Wagner et al. |
| 2016/0022987 A1 | 1/2016 | Zschaeck et al. |
| 2016/0022989 A1 | 1/2016 | Pfeifer |
| 2016/0038059 A1 | 2/2016 | Asada et al. |
| 2016/0045140 A1 | 2/2016 | Kitamura et al. |
| 2016/0089045 A1 | 3/2016 | Sadeghian-Motahar et al. |
| 2016/0106344 A1 | 4/2016 | Nazari |
| 2016/0120432 A1 | 5/2016 | Sridhar et al. |
| 2016/0121110 A1 | 5/2016 | Kent et al. |
| 2016/0128621 A1 | 5/2016 | Machado et al. |
| 2016/0129248 A1 | 5/2016 | Creasey et al. |
| 2016/0158542 A1 | 6/2016 | Ahmed |
| 2016/0158565 A1 | 6/2016 | Lee |
| 2016/0198998 A1 | 7/2016 | Rahimi et al. |
| 2016/0213924 A1 | 7/2016 | Coleman et al. |
| 2016/0220836 A1 | 8/2016 | Parks |
| 2016/0262685 A1 | 9/2016 | Wagner et al. |
| 2016/0263376 A1 | 9/2016 | Yoo et al. |
| 2016/0279435 A1 | 9/2016 | Hyde et al. |
| 2016/0287879 A1 | 10/2016 | Denison et al. |
| 2016/0039239 A1 | 11/2016 | Yoo et al. |
| 2016/0336722 A1 | 11/2016 | Taxter |
| 2016/0339239 A1 | 11/2016 | Yoo et al. |
| 2016/0361540 A9 | 12/2016 | Simon et al. |
| 2016/0375249 A1 | 12/2016 | Bonnet et al. |
| 2017/0014625 A1 | 1/2017 | Rosenbluth et al. |
| 2017/0027812 A1 | 2/2017 | Hyde et al. |
| 2017/0042467 A1 | 2/2017 | Herr et al. |
| 2017/0056238 A1 | 3/2017 | Yi et al. |
| 2017/0056643 A1 | 3/2017 | Herb et al. |
| 2017/0079597 A1 | 3/2017 | Horne |
| 2017/0080207 A1 | 3/2017 | Perez et al. |
| 2017/0095667 A1* | 4/2017 | Yakovlev .............. A61B 5/1118 |
| 2017/0113045 A1 | 4/2017 | Baldassano et al. |
| 2017/0157398 A1 | 6/2017 | Wong et al. |
| 2017/0165485 A1 | 6/2017 | Sullivan et al. |
| 2017/0132067 A1 | 8/2017 | Wong et al. |
| 2017/0224991 A1* | 8/2017 | Wingeier ........... A61N 1/36025 |
| 2017/0239415 A1 | 8/2017 | Hwang et al. |
| 2017/0246481 A1 | 8/2017 | Mishelevich |
| 2017/0266443 A1 | 9/2017 | Rajguru et al. |
| 2017/0274208 A1 | 9/2017 | Nagel et al. |
| 2017/0287146 A1 | 10/2017 | Pathak et al. |
| 2017/0312505 A1 | 11/2017 | Ahmed |
| 2017/0312512 A1 | 11/2017 | Creasey et al. |
| 2017/0312513 A1 | 11/2017 | Hershey et al. |
| 2017/0361093 A1 | 12/2017 | Yoo et al. |
| 2017/0368329 A1 | 12/2017 | Tyler et al. |
| 2018/0001086 A1 | 1/2018 | Bartholomew et al. |
| 2018/0001088 A1 | 1/2018 | Tass |
| 2018/0021576 A1 | 1/2018 | Wong et al. |
| 2018/0028841 A1 | 2/2018 | Konofagou et al. |
| 2018/0036535 A1 | 2/2018 | Wong et al. |
| 2018/0042654 A1 | 2/2018 | Ingvarsson et al. |
| 2018/0049676 A1 | 2/2018 | Griffiths et al. |
| 2018/0064344 A1 | 3/2018 | Nguyen |
| 2018/0064362 A1 | 3/2018 | Hennings et al. |
| 2018/0064944 A1 | 3/2018 | Grill et al. |
| 2018/0116546 A1 | 5/2018 | Pastoor et al. |
| 2018/0132757 A1 | 5/2018 | Kong et al. |
| 2018/0140842 A1 | 5/2018 | Olaighin et al. |
| 2018/0168905 A1 | 6/2018 | Goodall et al. |
| 2018/0169400 A1 | 6/2018 | Wong et al. |
| 2018/0214694 A1 | 8/2018 | Parramon |
| 2018/0221620 A1 | 8/2018 | Metzger |
| 2018/0235500 A1 | 8/2018 | Lee et al. |
| 2018/0236217 A1 | 8/2018 | Hamner et al. |
| 2018/0264263 A1 | 9/2018 | Rosenbluth et al. |
| 2018/0345020 A1 | 12/2018 | Ironi et al. |
| 2019/0001117 A1 | 1/2019 | Ben-David et al. |
| 2019/0001129 A1 | 1/2019 | Rosenbluth et al. |
| 2019/0001139 A1 | 1/2019 | Mishra et al. |
| 2019/0126047 A1 | 5/2019 | Kassiri Bidhendi et al. |
| 2019/0143098 A1 | 5/2019 | Kaplan et al. |
| 2019/0143111 A1 | 5/2019 | Hamner et al. |
| 2019/0143113 A1 | 5/2019 | Wong et al. |
| 2019/0167976 A1 | 6/2019 | Byers et al. |
| 2019/0269914 A1 | 9/2019 | Moaddeb et al. |
| 2019/0298998 A1 | 10/2019 | Coleman et al. |
| 2019/0321636 A1 | 10/2019 | Law et al. |
| 2019/0343462 A1* | 11/2019 | Grant .................. A61B 5/7221 |
| 2019/0374771 A1 | 12/2019 | Simon et al. |
| 2020/0023183 A1 | 1/2020 | Ollerenshaw et al. |
| 2020/0038654 A1 | 2/2020 | Doskocil et al. |
| 2020/0046968 A1 | 2/2020 | Herr et al. |
| 2020/0061378 A1 | 2/2020 | Ganguly et al. |
| 2020/0093400 A1 | 3/2020 | Hamner et al. |
| 2020/0139118 A1 | 5/2020 | John et al. |
| 2020/0147373 A1 | 5/2020 | Tamaki et al. |
| 2020/0155847 A1 | 5/2020 | Perez |
| 2020/0171269 A1 | 6/2020 | Hooper et al. |
| 2020/0171304 A1 | 6/2020 | Simon et al. |
| 2020/0179687 A1 | 6/2020 | Wong et al. |
| 2020/0197707 A1 | 6/2020 | Covalin |
| 2020/0215324 A1 | 7/2020 | Mantovani et al. |
| 2020/0221975 A1 | 7/2020 | Basta et al. |
| 2020/0254247 A1 | 8/2020 | Brezel et al. |
| 2020/0254251 A1 | 8/2020 | Wong et al. |
| 2020/0269046 A1 | 8/2020 | Page et al. |
| 2020/0276442 A1 | 9/2020 | Owen |
| 2020/0282201 A1 | 9/2020 | Doskocil |
| 2020/0289813 A1 | 9/2020 | Ito et al. |
| 2020/0289814 A1 | 9/2020 | Hamner et al. |
| 2020/0297999 A1 | 9/2020 | Pal |
| 2020/0316379 A1 | 10/2020 | Yoo et al. |

(56) References Cited

U.S. PATENT DOCUMENTS

| | | |
|---|---|---|
| 2020/0324104 A1 | 10/2020 | Labuschagne et al. |
| 2020/0338348 A1 | 10/2020 | Honeycutt et al. |
| 2020/0367775 A1 | 11/2020 | Buckley et al. |
| 2020/0405188 A1 | 12/2020 | Sharma et al. |
| 2020/0406022 A1 | 12/2020 | Sharma et al. |
| 2021/0016079 A1 | 1/2021 | Ekelem et al. |
| 2021/0031026 A1 | 2/2021 | Simon et al. |
| 2021/0031036 A1 | 2/2021 | Sharma et al. |
| 2021/0052883 A1 | 2/2021 | Wong et al. |
| 2021/0052897 A1 | 2/2021 | Bhadra et al. |
| 2021/0052900 A1 | 2/2021 | Pepin et al. |
| 2021/0060337 A1 | 3/2021 | Wybo et al. |
| 2021/0069507 A1 | 3/2021 | Gozani et al. |
| 2021/0100999 A1 | 4/2021 | Rosenbluth et al. |
| 2021/0101007 A1 | 4/2021 | Hamner et al. |
| 2021/0113834 A1 | 4/2021 | Wong et al. |
| 2021/0162212 A1 | 6/2021 | Kern et al. |
| 2021/0169684 A1 | 6/2021 | Black et al. |
| 2021/0187279 A1 | 6/2021 | Bouton et al. |
| 2021/0205619 A1 | 7/2021 | Wong et al. |
| 2021/0213283 A1 | 7/2021 | Yoo et al. |
| 2021/0220650 A1 | 7/2021 | Kassiri Bidhendi et al. |
| 2021/0244940 A1 | 8/2021 | Liberatore et al. |
| 2021/0244950 A1 | 8/2021 | Ironi et al. |
| 2021/0252278 A1 | 8/2021 | Hamner et al. |
| 2021/0260379 A1 | 8/2021 | Charlesworth et al. |
| 2021/0266011 A1 | 8/2021 | Chen et al. |
| 2021/0283400 A1 | 9/2021 | Hamner et al. |
| 2021/0289814 A1 | 9/2021 | Roubos-van den Hil et al. |
| 2021/0299445 A1 | 9/2021 | Rajguru et al. |
| 2021/0308460 A1 | 10/2021 | Wong et al. |
| 2021/0330547 A1 | 10/2021 | Moaddeb et al. |
| 2021/0330974 A1 | 10/2021 | Wong et al. |
| 2021/0353181 A1 | 11/2021 | Roh |
| 2021/0379374 A1 | 12/2021 | Hamner et al. |
| 2021/0379379 A1 | 12/2021 | Campean et al. |
| 2021/0402172 A1 | 12/2021 | Ross et al. |
| 2022/0001164 A1 | 1/2022 | Sharma et al. |
| 2022/0016413 A1 | 1/2022 | John et al. |
| 2022/0031245 A1 | 2/2022 | Bresler |
| 2022/0054820 A1 | 2/2022 | Turner |
| 2022/0054831 A1 | 2/2022 | McBride |
| 2022/0088373 A1 | 3/2022 | Burnett |
| 2022/0126095 A1 | 4/2022 | Rajguru et al. |
| 2022/0143391 A1 | 5/2022 | Vaishya et al. |
| 2022/0143392 A1 | 5/2022 | Labuschagne et al. |
| 2022/0143393 A1 | 5/2022 | Charlesworth et al. |
| 2022/0143402 A1 | 5/2022 | Oppenheim et al. |
| 2022/0203091 A1 | 6/2022 | Vysokov |
| 2022/0212007 A1 | 7/2022 | Rajguru et al. |
| 2022/0218991 A1 | 7/2022 | Moaddeb et al. |
| 2022/0220276 A1 | 7/2022 | Ziebell et al. |
| 2022/0233860 A1 | 7/2022 | Hamner et al. |
| 2022/0266011 A1 | 8/2022 | Hamner et al. |
| 2022/0266012 A1 | 8/2022 | Hamner et al. |
| 2022/0347461 A1 | 11/2022 | Campean et al. |
| 2022/0401721 A1 | 12/2022 | Jackson et al. |
| 2023/0009158 A1 | 1/2023 | Liberatore |
| 2023/0010696 A1 | 1/2023 | Pradeep |
| 2023/0062326 A1 | 3/2023 | Colachis et al. |
| 2023/0110185 A1 | 4/2023 | Mantovani et al. |
| 2023/0191115 A1 | 6/2023 | Blum et al. |
| 2023/0191126 A1 | 6/2023 | Kent et al. |
| 2023/0201584 A1 | 6/2023 | Rajguru et al. |
| 2023/0218897 A1 | 7/2023 | Wang et al. |
| 2023/0248962 A1 | 8/2023 | Zhang et al. |
| 2023/0277109 A1 | 9/2023 | Blum et al. |
| 2023/0277841 A1 | 9/2023 | Wang et al. |
| 2023/0285743 A1 | 9/2023 | Muccio |
| 2023/0293882 A1 | 9/2023 | Howe |
| 2023/0321430 A1 | 10/2023 | Ye et al. |
| 2023/0371846 A1 | 11/2023 | Sharma et al. |
| 2024/0058606 A1 | 2/2024 | Law et al. |
| 2024/0066286 A1 | 2/2024 | Yin et al. |
| 2024/0066287 A1 | 2/2024 | Siff |
| 2024/0090600 A1 | 3/2024 | Colachis et al. |
| 2024/0122797 A1 | 4/2024 | Moaddeb et al. |
| 2024/0123230 A1 | 4/2024 | Raghunathan |
| 2024/0157142 A1 | 5/2024 | Yeniel et al. |
| 2024/0189594 A1 | 6/2024 | Hamner et al. |
| 2024/0325727 A1 | 10/2024 | Hamner et al. |
| 2024/0325728 A1 | 10/2024 | Schulte et al. |

FOREIGN PATENT DOCUMENTS

| | | |
|---|---|---|
| CN | 1826154 | 8/2006 |
| CN | 101022849 | 8/2007 |
| CN | 101115524 | 1/2008 |
| CN | 101365373 | 2/2009 |
| CN | 101687093 | 3/2010 |
| CN | 101801453 | 8/2010 |
| CN | 102089031 | 6/2011 |
| CN | 102481394 | 5/2012 |
| CN | 202724457 | 2/2013 |
| CN | 103517732 | 1/2014 |
| CN | 103889503 | 6/2014 |
| CN | 104144729 | 11/2014 |
| CN | 104168951 | 11/2014 |
| CN | 104519960 | 4/2015 |
| CN | 105457158 | 4/2016 |
| CN | 105848710 | 8/2016 |
| CN | 106413805 | 2/2017 |
| CN | 106687161 | 5/2017 |
| CN | 106794347 | 5/2017 |
| CN | 107949421 | 4/2018 |
| CN | 108697890 | 10/2018 |
| DE | 102008042373 | 4/2010 |
| DE | 102009004011 | 7/2010 |
| EP | 0 000 759 | 2/1979 |
| EP | 0 725 665 | 1/1998 |
| EP | 1 062 988 | 12/2000 |
| EP | 1 558 333 | 5/2007 |
| EP | 1 727 591 | 4/2009 |
| EP | 2 383 014 | 11/2011 |
| EP | 2 291 115 | 9/2013 |
| EP | 2 801 389 | 11/2014 |
| EP | 3 020 448 | 5/2016 |
| EP | 2 029 222 | 3/2017 |
| EP | 2 780 073 | 9/2017 |
| EP | 1 951 365 | 10/2017 |
| EP | 3 154 627 | 4/2018 |
| EP | 2 827 771 | 5/2018 |
| EP | 3 184 143 | 7/2018 |
| EP | 3 075 412 | 12/2018 |
| EP | 3 349 712 | 7/2019 |
| EP | 3 503 960 | 3/2020 |
| EP | 3 352 846 | 7/2020 |
| EP | 3 493 874 | 8/2020 |
| EP | 3 409 200 | 9/2020 |
| EP | 3 427 793 | 11/2020 |
| EP | 3758595 | 1/2021 |
| EP | 3 641 876 | 4/2021 |
| EP | 3 679 979 | 6/2021 |
| EP | 3 402 404 | 7/2021 |
| EP | 3 562 541 | 7/2021 |
| EP | 3 675 795 | 8/2021 |
| EP | 3 100 765 | 1/2022 |
| EP | 3487578 | 12/2022 |
| EP | 4108292 | 12/2022 |
| EP | 3784337 | 6/2023 |
| EP | 4233990 | 8/2023 |
| EP | 3541279 | 9/2023 |
| EP | 3463550 | 3/2024 |
| EP | 3565631 | 4/2024 |
| EP | 4356952 | 4/2024 |
| EP | 3842094 | 5/2024 |
| ES | 2222819 | 3/2006 |
| ES | 2272137 | 6/2008 |
| GB | 2496449 | 5/2013 |
| JP | 2002-200178 | 7/2002 |
| JP | 2003-501207 | 1/2003 |
| JP | 2003-533299 | 11/2003 |
| JP | 2004-512104 | 4/2004 |
| JP | 2006-503658 | 2/2006 |

(56) References Cited

FOREIGN PATENT DOCUMENTS

| | | |
|---|---|---|
| JP | 2008-018235 | 1/2008 |
| JP | 2009-034328 | 2/2009 |
| JP | 2009-512516 | 3/2009 |
| JP | 2009-529352 | 8/2009 |
| JP | 2010-506618 | 3/2010 |
| JP | 2010-512926 | 4/2010 |
| JP | 2010-246745 | 11/2010 |
| JP | 2012-005596 | 1/2012 |
| JP | 2012-055650 | 3/2012 |
| JP | 2012-217565 | 11/2012 |
| JP | 2013-017609 | 1/2013 |
| JP | 2013-094305 | 5/2013 |
| JP | 5439921 B2 | 3/2014 |
| JP | 2015-514460 | 5/2015 |
| JP | 2016-511651 | 4/2016 |
| JP | 2018-038597 | 3/2018 |
| KR | 20130104446 | 9/2013 |
| WO | WO 87/01024 | 2/1987 |
| WO | WO 94/000187 | 1/1994 |
| WO | WO 94/017855 | 8/1994 |
| WO | WO 96/032909 | 10/1996 |
| WO | WO 98/043700 | 10/1998 |
| WO | WO 99/019019 | 4/1999 |
| WO | WO 00/015293 | 3/2000 |
| WO | WO 00/076436 | 12/2000 |
| WO | WO 01/087411 | 11/2001 |
| WO | WO 02/017987 | 3/2002 |
| WO | WO 02/34327 | 5/2002 |
| WO | WO 2004/037344 | 5/2004 |
| WO | WO 2004/108209 | 12/2004 |
| WO | WO 2005/007029 | 5/2005 |
| WO | WO 05/122894 | 12/2005 |
| WO | WO 2006/021820 | 3/2006 |
| WO | WO 2006/092007 | 9/2006 |
| WO | WO 2006/102724 | 10/2006 |
| WO | WO 07/092290 | 8/2007 |
| WO | WO 2007/092290 | 8/2007 |
| WO | WO 07/112092 | 10/2007 |
| WO | WO 08/045598 | 4/2008 |
| WO | WO 08/062395 | 5/2008 |
| WO | WO 2008/106174 | 9/2008 |
| WO | WO 09/153730 | 12/2009 |
| WO | WO 2010/014260 | 2/2010 |
| WO | WO 10/111321 | 9/2010 |
| WO | WO 10/141155 | 12/2010 |
| WO | WO 11/119224 | 9/2011 |
| WO | WO 2011/144883 | 11/2011 |
| WO | WO 2011/149656 | 12/2011 |
| WO | WO 12/040243 | 3/2012 |
| WO | WO 13/071307 | 5/2013 |
| WO | WO 13/074809 | 5/2013 |
| WO | WO 13/173727 | 11/2013 |
| WO | WO 14/043757 | 3/2014 |
| WO | WO 14/053041 | 4/2014 |
| WO | WO 2014/070999 | 5/2014 |
| WO | WO 14/089549 | 6/2014 |
| WO | WO 14/093964 | 6/2014 |
| WO | WO 2014/113813 | 7/2014 |
| WO | WO 14/146082 | 9/2014 |
| WO | WO 14/151431 | 9/2014 |
| WO | WO 14/153201 | 9/2014 |
| WO | WO 14/207512 | 12/2014 |
| WO | WO 15/033152 | 3/2015 |
| WO | WO 15/039206 | 3/2015 |
| WO | WO 15/039244 | 3/2015 |
| WO | WO 15/042365 | 3/2015 |
| WO | WO 15/079319 | 6/2015 |
| WO | WO 15/095880 | 6/2015 |
| WO | WO 2015/085880 | 6/2015 |
| WO | WO 15/128090 | 9/2015 |
| WO | WO 15/138981 | 9/2015 |
| WO | WO 2015/138981 | 9/2015 |
| WO | WO 15/164706 | 10/2015 |
| WO | WO 2015/187712 | 12/2015 |
| WO | WO 16/007093 | 1/2016 |
| WO | WO 16/019250 | 2/2016 |
| WO | WO 16/094728 | 6/2016 |
| WO | WO 16/102958 | 6/2016 |
| WO | WO 16/110804 | 7/2016 |
| WO | WO 16/128985 | 8/2016 |
| WO | WO 16/149751 | 9/2016 |
| WO | WO 16/166281 | 10/2016 |
| WO | WO 16/179407 | 11/2016 |
| WO | WO 2016/176668 | 11/2016 |
| WO | WO 16/189422 | 12/2016 |
| WO | WO 16/195587 | 12/2016 |
| WO | WO 2016/201366 | 12/2016 |
| WO | WO 17/004021 | 1/2017 |
| WO | WO 17/010930 | 1/2017 |
| WO | WO 2017/023864 | 2/2017 |
| WO | WO 17/044904 | 3/2017 |
| WO | WO 2017/053847 | 3/2017 |
| WO | WO 17/062994 | 4/2017 |
| WO | WO 17/086798 | 5/2017 |
| WO | WO 17/088573 | 6/2017 |
| WO | WO 2017/132067 | 8/2017 |
| WO | WO 17/199026 | 11/2017 |
| WO | WO 17/208167 | 12/2017 |
| WO | WO 17/209673 | 12/2017 |
| WO | WO 17/210729 | 12/2017 |
| WO | WO 17/221037 | 12/2017 |
| WO | WO 2018/009680 | 1/2018 |
| WO | WO 18/028170 | 2/2018 |
| WO | WO 18/028220 | 2/2018 |
| WO | WO 18/028221 | 2/2018 |
| WO | WO 2018/039458 | 3/2018 |
| WO | WO 18/093765 | 5/2018 |
| WO | WO 18/106839 | 6/2018 |
| WO | WO 18/112164 | 6/2018 |
| WO | WO 2018/106839 | 6/2018 |
| WO | WO 2018119220 | 6/2018 |
| WO | WO 2018/187241 | 10/2018 |
| WO | WO 19/005774 | 1/2019 |
| WO | WO 19/014250 | 1/2019 |
| WO | WO 19/028000 | 2/2019 |
| WO | WO 19/046180 | 3/2019 |
| WO | WO 19/082180 | 6/2019 |
| WO | WO 2019/143790 | 7/2019 |
| WO | WO 19/169240 | 9/2019 |
| WO | WO 19/202489 | 10/2019 |
| WO | WO 2019/213433 | 11/2019 |
| WO | WO 2020/006048 | 1/2020 |
| WO | WO 20/068830 | 4/2020 |
| WO | WO 2020/069219 | 4/2020 |
| WO | WO 2020/086726 | 4/2020 |
| WO | WO 20/131857 | 6/2020 |
| WO | WO 20/185601 | 9/2020 |
| WO | WO 21/005584 | 1/2021 |
| WO | WO 21/055716 | 3/2021 |
| WO | WO 21/062345 | 4/2021 |
| WO | WO 21/127422 | 6/2021 |
| WO | WO 21/228128 | 11/2021 |
| WO | WO 2021/236815 | 11/2021 |
| WO | WO 21/252292 | 12/2021 |
| WO | WO 2022/090834 | 5/2022 |
| WO | WO 2022/221858 | 10/2022 |
| WO | WO 2022/235607 | 11/2022 |
| WO | WO 2023/283568 | 1/2023 |
| WO | WO 2023/014499 | 2/2023 |
| WO | WO 2023/015158 | 2/2023 |
| WO | WO 2023/015159 | 3/2023 |
| WO | WO 2023/156391 | 8/2023 |
| WO | WO 2023/163300 | 8/2023 |
| WO | WO 2023/191236 | 10/2023 |
| WO | WO 2023/196578 | 10/2023 |
| WO | WO 2023/222911 | 11/2023 |
| WO | WO 2024/083685 | 4/2024 |

OTHER PUBLICATIONS

Barath et al., 2020, Brain metabolic changes with longitudinal transcutaneous afferent patterned stimulation in essential tremor

(56) References Cited

OTHER PUBLICATIONS subjects, Tremor and Other Hyperkinetic Movements, 10(1):52, pp. 1-10.
Barbaud et al.; Improvement in essential tremor after pure sensory stroke due to thalamic infarction; European neurology; 46; pp. 57-59; Jul. 2001.
Barrios et al.: BCI algorithms for tremor identification, characterization and tracking; Seventh Framework Programme, EU; Contract No. FP7-ICT-2007-224051 (v3.0); 57 pgs.; Jul. 10, 2011.
Bartley et al.; Neuromodulation for overactive bladder; Nature Reviews Urology; 10; pp. 513-521; Sep. 2013.
Benabid et al.; A putative generalized model of the effects and mechanism of action of high frequency electrical stimulation of the central nervous system; Acta Neural Belg; 105(3); pp. 149-157; Sep. 2005.
Bergquist et al.: Motor unit recruitment when neuromuscular electrical stimulation is applied over a nerve trunk compared with a muscle belly: quadriceps femoris, Journal of Applied Physiology; vol. 113, No. 1, pp. 78-89; Jul. 2012.
Bergquist et al.; Motor unit recruitment when neuromuscular electrical stimulation is applied over a nerve trunk compared with a muscle belly: triceps surae, Journal of Applied Physiology; vol. 110, No. 3, pp. 627-637; Mar. 2011.
Bijelic et al.: E Actitrode®: The New Selective Stimulation Interface for Functional Movements in Hemiplegic Patients; Serbian Journal of Electrical Engineering; 1(3); pp. 21-28; Nov. 2004.
Birdno et al.; Pulse-to-pulse changes in the frequency of deep brain stimulation affect tremor and modeled neuronal activity.; Journal of Neurophysiology; 98; pp. 1675-1684; Jul. 2007.
Birdno et al.; Response of human thalamic neurons to high-frequency stimulation.; PloS One; 9(5); 10 pgs.; May 2014.
Birgersson et al.; Non-invasive bioimpedance of intact skin: mathematical modeling and experiments; Physiological Measurement; 32(1); pp. 1-18; Jan. 2011.
Bohling et al.; Comparison of the stratum corneum thickness measured in vivo with confocal Raman spectroscopy and confocal reflectance microscopy; Skin research and Technology; 20(1); pp. 50-47; Feb. 2014.
Bonaz, B., V. Sinniger, and S. Pellissier. "Vagus nerve stimulation: a new promising therapeutic tool in inflammatory bowel disease." Journal of internal medicine 282.1 (2017): 46-63.
Bowman et al.; Effects of waveform parameters on comfort during transcutaneous neuromuscular electrical stimulation; Annals of Biomedical Engineering; 13(1); pp. 59-74; Jan. 1985.
Bratton et al.; Neural regulation of inflammation: no neural connection from the vagus to splenic sympathetic neurons; Exp Physiol 97.11 (2012); pp. 1180-1185.
Brillman et al., 2022, Real-world evidence of transcutaneous afferent patterned stimulation for essential tremor, Tremor and Other Hyperkinetic Movements, 12(1):27, pp. 1-11.
Brittain et al.; Tremor suppression by rhythmic transcranial current stimulation; Current Biology; 23; pp. 436-440; Mar. 2013.
Britton et al.; Modulation of postural tremors at the wrist by supramaximal electrical median nerve shocks in ET, PD, and normal subjects mimicking tremor; J Neurology, Neurosurgery, and Psychiatry; 56(10); pp. 1085-1089; Oct. 1993.
Buschbacher et al.; Manual of nerve conduction series; 2nd edition; Demos Medical Publishing, LLC; 2006.
Cagnan et al.; Phase dependent modulation of tremor amplitude in essential tremor through thalamic stimulation; Brain; 136(10); pp. 3062-3075; Oct. 2013.
Campero et al.; Peripheral projections of sensory fasicles in the human superificial radial nerve; Brain; 128(Pt 4); pp. 892-895; Apr. 2005.
Chen et al.; A web-based system for home monitoring of patients with Parkinson's disease using wearable sensors; IEEE Trans on Bio-Medical Engineering; 58(3); pp. 831-836; Mar. 2011.
Choi, Jong Bo, et al. "Analysis of heart rate variability in female patients with overactive bladder." Urology 65.6 (2005): 1109-1112.
Clair et al.; Postactivation depression and recovery of reflex transmission during repetitive electrical stimulation of the human tibial nerve, Journal of Neurophysiology; vol. 106, No. 1; pp. 184-192; Jul. 2011.
Clar et al.; Skin impedance and moisturization; J. Soc. Cosmet. Chem.; 26; pp. 337-353; 1975; presented at IFSCC Vilith Int'l Congresson Cosmetics Quality and Safety in London on Aug. 26-30, 1974.
Constandinou et al.; A Partial-Current-Steering Biphasic Stimulation Driver for Vestibular Prostheses; IEEE Trans on Biomedical Circuits and Systems; 2(2); pp. 106-113; Jun. 2008.
Daneault et al.; Using a smart phone as a standalone platform for detection and monitoring of pathological tremors; Frontiers in Human Neuroscience; vol. 6, article 357; 12 pgs.; Jan. 2012.
Deuschl et at; Consensus statement of the Movement Disorder Society on Tremor. Ad Hoc Scientific Committee., Movement Disorders, vol. 13 Suppl 3, pp. 2-23; 1998.
Di Giovangiulio et al.; The Neuromodulation of the intestinal immune system and its relevance in inflammatory bowel disease; Fronteir's in Immunology; vol. 6; Article 590; Nov. 2015.
Dideriksen et al.; EMG-based characterization of pathological tremor using the iterated Hilbert transform; IEEE transactions on Biomedical Engineering; 58(10); pp. 2911-2921; Oct. 2011.
Dosen et al.: Tremor suppression using electromyography and surface sensory electrical stimulation; Converging Clinical and Engineering Research on Neurorehabilitation; vol. 1 (Siosystems & Biorobotics Series); pp. 539-543; Feb. 2013.
Doucet et al.; Neuromuscular electrical stimulation for skeletal muscle function; The Yale Journal of Biology and Medicine; 85(2); pp. 201-215; Jun. 2012.
Ferreira et al., 2019, MDS evidence-based review of treatments for essential tremor, Movement Disorders, 34(7):950-958.
Fiorentino et al., 2011, Self calibrating wearable active running asummetry measurement and correction, Journal of Control Engineering and Applied Informatics, 13(2):3-8.
Fuentes et al.; Restoration of locomotive function in Parkinson's disease by spinal cord stimulation: mechanistic approach, Eur J Neurosci, vol. 32, pp. 1100-1108; Oct. 2010 (author manuscript; 19 pgs.).
Fuentes et al.; Spinal cord stimulation restores locomotion in animal models of Parkinson's disease; Science; 323; pp. 1578-1582; Mar. 2009.
Gallego et al.; A neuroprosthesis for tremor management through the control of muscle co-contraction; Journal of Neuroengineering and Rehabilitation; vol. 10; 36; (13 pgs); Apr. 2013.
Gallego et al.; Real-time estimation of pathological tremor parameters from gyroscope data.; Sensors; 10(3); pp. 2129-2149; Mar. 2010.
Gallego et al; A soft wearable robot for tremor assessment and suppression; 2011 IEEE International Conference on Robotics and Automation; Shanghai International Conference Center; pp. 2249-2254; May 9-13, 2011.
Gao; Analysis of amplitude and frequency variations of essential and Parkinsonian tremors; Medical & Biological Engineering & Computing; 42(3); pp. 345-349; May 2004.
Garcia et al.; Modulation of brainstem activity and connectivity by respiratory-gated auricular vagal afferent nerve stimulation in migraine patients; Pain; International Association for the Study of Pain; 2017.
Garcia-Rill, E., et al. "Arousal, motor control, and Parkinson's disease." Translational neuroscience 6.1 pp. 198-207 (2015).
Giuffridda et al.; Clinically deployable Kinesia technology for automated tremor assessment.; Movement Disorders; 24(5); pp. 723-730; Apr. 2009.
Gracanin et al.; Optimal stimulus parameters for minimum pain in the chronic stimulatin of innervated muscle; Archives of Physical Medicine and Rehabilitation; 56(6); pp. 243-249; Jun. 1975.
Gupta et al., 2021, Exploring essential tremor: results from a large online survey, Clinical Parkinsonism & Related Disorders, 5:100101, 4 pp.
Haeri et al.; Modeling the Parkinson's tremor and its treatments; Journal of Theorectical Biology; 236(3); pp. 311-322; Oct. 2005.

(56) References Cited

OTHER PUBLICATIONS

Halonen et al.; Contribution of cutaneous and muscle afferent fibres to cortical SEPs following median and radial nerve stimulation in man; Electroenceph. Clin. Neurophysiol.; 71(5); pp. 331-335; Sep.-Oct. 1988.
Hao et al.; Effects of electrical stimulation of cutaneous afferents on corticospinal transmission of tremor signals in patients with Parkinson's disease; 6th International Conference on Neural Engineering; San Diego, CA; pp. 355-358; Nov. 2013.
Haubenberger et al., 2018, Essential Tremor, The New England Journal of Medicine, 378:1802-1810 and Supplementary Appendix.
Hauptmann et al.; External trial deep brain stimulation device for the application of desynchronizing stimulation techniques; Journal of Neural Engineering; 6; 12 pgs.; Oct. 2009.
Heller et al.; Automated setup of functional electrical stimulation for drop foot using a novel 64 channel prototype stimulator and electrode array: Results from a gait-lab based study; Medical Engineering & Physic; 35(1); pp. 74-81; Jan. 2013.
Hellwig et al., Feb. 17, 2001, Tremor-correlated cortical activity in essential tremor, The Lancet, 357:519-523.
Henry Dreyfuss Associates; The Measure of Man and Woman: Human Factors in Design (Revised Edition); John Wiley & Sons, New York; pp. 10-11 and 22-25; Dec. 2001.
Hernan, Miguel, et al. "Alcohol Consumption and the Incidence of Parkinson's Disease." May 15, 2003. Annals of Neurology. vol. 54. pp. 170-175.
Hernandez-Martin et al., 2021, High-fidelity transmission of high-frequency burst stimuli from peripheral nerve to thalamic nuclei in children with dystonia, Scientific Reports, 11:8498, 9 pp.
Hua et al.; Posture-related oscillations in human cerebellar thalamus in essential tremor are enabled by voluntary motor circuits; J Neurophysiol; 93(1); pp. 117-127; Jan. 2005.
Huang, et al.; Theta burst stimulation report of the human motor cortex; Neuron, vol. 45, 201-206, Jan. 20, 2005.
Hubeaux, Katelyne, et al. "Autonomic nervous system activity during bladder filling assessed by heart rate variability analysis in women with idiopathic overactive bladder syndrome or stress urinary incontinence." The Journal of urology 178.6 (2007): 2483-2487.
Hubeaux, Katelyne, et al. "Evidence for autonomic nervous system dysfunction in females with idiopathic overactive bladder syndrome." Neurourology and urodynamics 30.8 (2011): 1467-1472.
Inoue et al. "Stretchable human interface using a conductive silicone elastomer containing silver fillers." Consumer Electronics, 2009. ISCE'09. IEEE 13th International Symposium on. IEEE, 2009.
Isaacson et al., 2020, Prospective home-use study on non-invasive neuromodulation therapy for essential tremor, Tremor and Other Hyperkinetic Movements, 10(1):29, pp. 1-16.
Jacks et al.; Instability in human forearm movements studied with feed-back-controlled electrical stimulation of muscles; Journal of Physiology; 402; pp. 443-461; Aug. 1988.
Jobges et al.; Vibratory proprioceptive stimulation affects Parkinsonian tremor; Parkinsonism & Related Disorders; 8(3); pp. 171-176; Jan. 2002.
Joundi et al.; Rapid tremor frequency assessment with the iPhone accelerometer.; Parkinsonism & Related Disorders; 17(4); pp. 288-290; May 2011.
Kim et al.: Adaptive control of movement for neuromuscular stimulation-assisted therapy in a rodent model; IEEE Trans on Biomedical Engineering,; 56(2); pp. 452-461; Feb. 2009.
Krauss et al.; Chronic spinal cord stimulation in medically intractable orthostatic tremor; J Neurol Neurosurg Psychiatry; 77(9); pp. 1013-1016; Sep. 2006.
Krishnamoorthy et al., 2008, Gait Training After Stroke: A Pilot Study Combining a Gravity-Balanced Orthosis, Functional Electrical Stimulation, and Visual Feedback, Journal of Neurologic Physical Therapy, 32(4):192-202.

Kuhn et al.; Array electrode design for transcutaneous electrical stimulation a simulation study; Medical Engineering & Physics; 31 (8); pp. 945-951; Oct. 2009.
Kuhn et al.; The Influence of Electrode Size on Selectivity and Comfort in Transcutaneous Electrical Stimulation of the Forearm; Neural Systems and Rehabilitation Engineering, IEEE Transactions on; 18(3); pp. 255-262; Jun. 2010.
Kunz, Patrik, et al. "5 kHz transcranial alternating current stimulation: lack of cortical excitability changes when grouped in a theta burst pattern." Frontiers in Human Neuroscience 10 (2016): 683.
Lagerquist et al.: Influence of stimulus pulse width on M-waves, H-reflexes, and torque during tetanic low-intensity neuromuscular stimulation, Muscle & Nerve, 42(6), pp. 886-893; Dec. 2010.
Laroy et al.; The sensory innervation pattern of the fingers; J. Neurol.; 245 (5); pp. 294-298; May 1998.
Lee et al.; Resetting of tremor by mechanical perturbations: A comparison of essential tremor and parkinsonian tremor; Annals of Nuerology; 10(6); pp. 523-531; Dec. 1981.
Legon et al.; Pulsed ultrasound differentially stimulates somatosensory circuits in humans as indicated by EEG and fMRI; PLoS ONE; 7(12); e51177; 14 pgs.; Dec. 2012.
Liao, Wen-Chien, et al. "A noninvasive evaluation of autonomic nervous system dysfunction in women with an overactive bladder." International Journal of Gynecology & Obstetrics 110.1 (2010): 12-17.
Lin et al., 2018, Noninvasive neuromodulation inessential tremor demonstrates relief in a sham-controlled pilot trial, Movement Disorders, 33(7):1182-1183.
Llinas et al., Dec. 21, 1999, Thalamocortical dysrhythmia: a neurological and neuropsychiatric syndrome characterized by magnetoencephalography, PNAS, 96(26):15222-15227.
Lourenco et al.; Effects produced in human arm and forearm motoneurones after electrical stimulation of ulnar and median nerves at wrist level; Experimental Brain Research; 178(2); pp. 267-284; Apr. 2007.
Lyons et al., 2021, Essential tremor in adult patients, International Essential Tremor Foundation, 16 pp.
Malek et al.; The utility of electromyography and mechanomyography for assessing neuromuscular function: a noninvasive approach; Phys Med Rehabil in N Am; 23(1); pp. 23-32; Feb. 2012.
Mamorita et al.; Development of a system for measurement and analysis of tremor using a three-axis accelerometer; Methods Inf Med; 48(6); pp. 589-594; epub Nov. 2009.
Maneski et al.; Electrical Stimulation for suppression of pathological tremor; Med Biol Eng Comput; 49(10); pp. 1187-1193; Oct. 2011.
Marsden et al.; Coherence between cerebellar thalamus, cortex and muscle in man; Brain; 123; pp. 1459-1470; Jul. 2000.
Marshall, Ryan, et al. "Bioelectrical stimulation for the reduction of inflammation in inflammatory bowel disease." Clinical Medicine Insights: Gastroenterology 8 (2015): CGast-S31779.
McAuley et al.; Physiological and pathological tremors and rhythmic central motor control; Brain; 123(Pt 8); pp. 1545-1567; Aug. 2000.
McIntyre et al.; Finite element analysis of current-density and electric field generated by metal microelectrodes; Annals of Biomedical Engineering; 29(3); pp. 227-235; Mar. 2001.
Meekins et al.; American Association of Neuromuscular & Electrodiagnostic Medicine evidenced-based review: use of surface electromyography in the diagnosis and study of neuromuscular disorders; Muscle Nerve 38(4); pp. 1219-1224; Oct. 2008.
Mehnert, Ulrich, et al. "Heart rate variability: an objective measure of autonomic activity and bladder sensations during urodynamics." Neurourology and urodynamics 28.4 (2009): 313-319.
Miguel et al.; Alcohol consumption and the incidence of Parkinson's disease; Ann. Neurol.; 54(2); pp. 170-175; May 15, 2003.
Miller et al.; Multiplexed microneedle-based biosensor array for characterization of metabolic acidosis; Talanta; 88; pp. 739-742; Jan. 2012 (author manuscript; 13 pgs.).
Miller et al.; Neurostimulation in the treatment of primary headaches; Pract Neurol; Apr. 11, 2016;16:pp. 362-375.

(56) References Cited

OTHER PUBLICATIONS

Milne et al.; Habituation to repeated in painful and non-painful cutaneous stimuli: A quantitative psychophysical study; Experimental Brain Research; 87(2); pp. 438-444; Nov. 1991.
Mommaerts et al.; Excitation and nerve conduction; in Comprehensive Human Physiology; Springer Berlin Heidelberg; Chap. 13; pp. 283-294; Mar. 1996.
Mones et al.; The response of the tremor of patients with Parkinsonism to peripheral nerve stimulation; J Neurology, Neurosurgery, and Psychiatry; 32(6); pp. 512-518; Dec. 1969.
Morgante et al.: How many parkinsonian patients are suitable candidates for deep brain stimulation of subthalamic nucleus?; Results of a Questionnaire, Partkinsonism Relat Disord; 13; pp. 528-531; Dec. 2007.
Munhoz et al; Acute effect of transcutaneous electrical nerve stimulation on tremor; Movement Disorders; 18(2); pp. 191-194; Feb. 2003.
Nardone et al.; Influences of transcutaneous electrical stimulation of cutaneous and mixed nerves on subcortical somatosensory evoked potentials; Electroenceph. Clin. Neurophysiol.; 74(1); pp. 24-35; Jan.-Feb. 1989.
Nonis et al.; Evidence of activation of vagal afferents by non-invasive vagus nerve stimulation: An electrophysiological study in healthy volunteers; Cephalalgia; pp. 1285-1293; vol. 37(13); Mar. 28, 2017.
Pahwa et al., 2018, An acute randomized controlled trial of noninvasive peripheral nerve stimulation in essential tremor, Neuromodulation, 22:537-545.
Peng et al., 2015, Flexible dry electrode based on carbon nanotube/plymer hybrid micorpillars for biopotential recording, Sensor and Actuatora A: Physical, 235:48-65.
Perez et al.; Patterned Sensory Stimulation Induces Plasticity in Reciprocal Ia Inhibition in Humans; The Journal of Neuroscience; 23(6); pp. 2014-2018; Mar. 2003.
Perez-Reyes, Jan. 2003, Molecular physiology of low-voltage-activated T-type calcium channels, Physiol. Rev. 83:117-161.
Perlmutter et al.; Deep brain stimulation; Ann Rev Neurosci; 29; pp. 229-257; Jul. 2006.
Popovic-Bijelic et al. "Multi-field surface electrode for selective electrical stimulation." Artificial organs 29.6 (2005): 448-452.
Prochazka et al.; Attenuation of pathological tremors by functional electrical stimulation I: Method; Annals of Biomedical Engineering; 20(2); pp. 205-224; Mar. 1992.
Pulliam et al.; Continuous in-home monitoring of essential tremor; Parkinsonism Relat Disord; 20(1); pp. 37-40; Jan. 2014.
Quattrini et al.; Understanding the impact of painful diabetic neuropathy; Diabetes/Metabolism Research and Reviews; 19, Suppl. 1; pp. S2-S8; Jan.-Feb. 2003.
Rocon et al.; Design and validation of a rehabilitation robotic exoskeleton for tremor assessment and suppression; IEEE Trans Neural Sys and Rehab Eng.; 15(3); pp. 367-378; Sep. 2007.
Sigrist et al., 2012. Augmented visual, auditory, haptic, and multimodal feedback in motor learning: A review. Psychonomic Bulletin & Review, 20(1):21-53.
Silverstone et al.; Non-Invasive Neurostimulation in the Control of Familial Essential Tremor Using the Synaptic Neuromodulator; Conference Proceedings, International Functional Electrical Stimulation Society (IFES); Ed. Paul Meadows; 3 pgs.; May 1999.
Singer et al.; The effect of EMG triggered electrical stimulation plus task practice on arm function in chronic stroke patients with moderate-severe arm deficits; Restor Neurol Neurosci; 31(6); pp. 681-691; Oct. 2013.
Solomonow et al., 1998, Studies toward spasticity suppression with hight frequency electrical stimulation, Orthopedics, 7(8):1284-1288.
Straube et al.; Treatment of chronic migraine with transcutaneous stimulation of the auricular branch of the vagal nerve (auricular t-VNS): a randomized, monocentric clinical trial; The Journal of Headache and Pain (2015) 16:63.

Takanashi et al.; A functional MRI study of somatotopic representation of somatosensory stimulation in the cerebellum; Neuroradiology; 45(3); pp. 149-152; Mar. 2003.
Tass et al.; Coordinated reset has sustained aftereffects in Parkinsonian monkeys; Ann Neurol; 72(5); pp. 816-820; Nov. 2012.
Tass et al.; Counteracting tinnitus by acoustic coordinated reset neuromodulation; Restorative neurology and Neuroscience; 30(2); pp. 137-159; Apr. 2012.
Tass; A Model of desynchronizing deep brain stimulation with a demand-controlled coordinated reset of neural subpopulations; Bioi Cybern; 89(2); pp. 81-88; Aug. 2003.
Thomas et al.; A review of posterior tibial nerve stimulation for faecal incontinence; Colorectal Disease; 2012 The Association of Coloproctology of Great Britain and Ireland. 15, pp. 519-526; Jun. 25, 2012.
Tolosa et al.; Essential tremor: treatment with propranolol; Neurology; 25(11); pp. 1041; Nov. 1975.
Tracey; The inflammatory reflex; Nature; vol. 420; pp. 853-859; Dec. 19/26, 2002.
Treager; Interpretation of skin impedance measurements; Nature; 205; pp. 600-601; Feb. 1965.
Valente; Novel methods and circuits for field shaping in deep brain stimulation; Doctoral thesis, UCL (University College London); 222 pgs.; 2011.
Vitton et al.; Transcutaneous posterior tibial nerve stimulation for fecalIncontinence in inflammatory bowel disease patients: a therapeutic option?; Inflamm Bowel Dis; vol. 15, No. 3, Mar. 2009; pp. 402-405.
Von Lewinski et al.; Efficacy of EMG-triggered electrical arm stimulation in chronic hemiparetic stroke patients; Restor Neurol Neurosci; 27(3); pp. 189-197; Jun. 2009.
Wardman et al.; Subcortical, and cerebellar activation evoked by selective stimulation of muscle and cataneous afferents: an fMRI study; Physiol. Rep.; 2(4); pp. 1-16; Apr. 2014.
Wiestler et al.; Integration of sensory and motor representations of single fingers in the human; J. Neurophysiol.; 105(6); pp. 3042-3053; Jun. 2011.
Woldag et al.; Evidence-based physiotherapeutic concepts for improving arm and hand function in stroke patients R A review; J Neurol; 249(5); pp. 518-528; May 2002.
Woolf et al.; Peripheral nerve injury triggers central sprouting of myelinated afferents; Nature; 355(6355); pp. 75-78; Jan. 1992.
Yarnitsky et al.; Nonpainful remote electrical stimulation alleviates episodic migraine pain; Neurology 88; pp. 1250-1255; Mar. 28, 2017.
Yeh et al., "Intensity sensitive modulation effect of theta burst form of median nerve stimulation on the monosynaptic spinal reflex." Neural plasticity 2015 (2015) in 8 pages.
Yilmaz, Ozlem O., et al. "Efficacy of EMG-biofeedback in knee osteoarthritis." Rheumatology international 30.7 (2010): 887-892.
Zhang et al.; Neural oscillator based control for pathological tremor suppression via functional electrical stimulation; Control Engineering Practice; 19(1); pp. 74-88; Jan. 2011.
Zorba et al.; Overactive bladder and the pons; Rize University, Medical Faculty, Department of Urology; 123-124; Undated.
Zwarts et al.; Multichannel surface EMG: basic aspects and clinical utility; Muscle Nerve; 28(1); pp. 1-17; Jul. 2003.
Knutson et al., Nov. 2015, Neuromuscular electrical stimulation for motor restoration in hemiplegia, Phys. Med. Rehabil. Clin. N. Am., 26(4):729-745.
Amarenco et al. "Urondynamic Effect of Acute Transcutaneous Posterior Tibial Nerve Stimulation in Overactive Bladder" Journal of Urology vol. 169, 2210-2215 (Jun. 2003).
Buschbacher et al.; Manual of nerve conduction series; 2nd edition; Demos Medical Publishing, LLC; 2006 (part 2, p. #143 to #299).
Fred E. Govier, et al., "Percutaneous Afferent Neuromodulation for the Refractory Overactive Bladder: Results of a Multicenter Study," 165 J. Urology 1193-1198 (Apr. 2001).
H.C. Klingler, et al., "Use of Peripheral Neuromodulation of the S3 Region for Treatment of Detrusor Overactivity: A Urodynamicbased Study," Urology 56:766-771, 2000.

(56) References Cited

OTHER PUBLICATIONS

Knutson et al., Neuromuscular Electrical Stimulation for Motor Restoration in Hemiplegia. Phys Med Rehabil Clin N A,. Nov. 2015; 26(4): 729-745. Published online Aug. 14, 2015. Doi: 10.1016/j.pmr.2015.06.002.

Michael R. Van Balken, et al., "Posterior Tibial Nerve Stimulation as Neuromodulative Treatment of Lower Urinary Track Dysfunction," 166 J. Urology 914-918 (Sep. 2001).

Popovi Maneski et al.; Electrical stimulation for the suppression of pathological tremor; Medical & Biological Engineering & Computing; 49(10); pp. 1187-1193; Oct. 2011.

Wallerberger, Apr. 4, 2019, Efficient Estimation of Autocorrelation Spectra, ArXiv.org, https://arxiv.org/abs/1810.05079.

Cala Trio Health Care Professional Guide (Jul. 2020).

Cala Trio Health Care Professional Guide (Nov. 2019).

Chang, M.D., Qwang-Yuen et al., Effect of Electroacupuncture and Transcutaneous Electrical Nerve Stimulation at Hegu (LI.4) Acupuncture Point on the Cutaneous Reflect, 27 Acupuncture & Electro-Therapeutics Res., Int. J. 191-202 (2002).

Javidan, et al, Attenuation of Pathological Tremors by Functional Electrical Stimulation II: Clinical Evaluation, 20 Annals of Biomedical Engineering 225 (1992).

PTAB-IPR2024-00732—Exhibit 1002—Declaration of John Laughlin, M. Eng., P.E., in 109 pages.

PTAB-IPR2024-00732—Petition for Inter Partes Review of U.S. Pat. No. 10,786,669, filed Mar. 29, 2024, in 101 pages.

PTAB-IPR2024-00743—Exhibit 1002—Declaration of John Laughlin, M. Eng., P.E., in 102 pages.

PTAB-IPR2024-00743—Petition for Inter Partes Review of U.S. Pat. No. 11,628,300, filed Mar. 29, 2024, in 113 pages.

\* cited by examiner

CONNECTION QUALITY DETERMINATION FOR WEARABLE NEUROSTIMULATION SYSTEMS

REFERENCE TO RELATED APPLICATIONS

This application claims the benefit under 35 U.S.C. § 119 (e) to U.S. Prov. App. No. 62/886,218 filed on Aug. 13, 2019, which is hereby incorporated by reference in its entirety.

BACKGROUND

Field

Embodiments of the invention relate generally to systems, devices, and methods for stimulating nerves, and more specifically relate to system, devices, and methods for electrically stimulating peripheral nerve(s) to treat various disorders, as well as signal processing systems and methods for enhancing diagnostic and therapeutic protocols relating to the same.

Description of the Related Art

A wide variety of modalities can be utilized to neuromodulate peripheral nerves. For example, electrical energy can be delivered transcutaneously or percutaneously via electrodes on the skin surface with neurostimulation systems to stimulate peripheral nerves, such as the median, radial, and/or ulnar nerves in the upper extremities; the tibial, saphenous, and/or peroneal nerve in the lower extremities; or the auricular vagus, tragus, trigeminal, occipital, or cranial nerves on the head or ear, as non-limiting examples. Stimulation of these nerves has been shown to provide therapeutic benefit across a variety of diseases, including but not limited to movement disorders (including but not limited to essential tremor, Parkinson's tremor, orthostatic tremor, and multiple sclerosis), urological disorders, gastrointestinal disorders, cardiac diseases, and inflammatory diseases, mood disorders (including but not limited to depression, bipolar disorder, dysthymia, and anxiety disorder), pain syndromes (including but not limited to migraines and other headaches, trigeminal neuralgia, fibromyalgia, complex regional pain syndrome), among others. A number of conditions, such as tremors, can be treated through some form of transcutaneous, percutaneous, or other implanted forms of peripheral nerve stimulation.

SUMMARY

Systems with compact, ergonomic form factors are needed to enhance efficacy, compliance, and/or comfort when using non-invasive or wearable neuromodulation devices. In several embodiments, neuromodulation systems and methods are provided that enhance or inhibit nerve impulses and/or neurotransmission, and/or modulate excitability of nerves, neurons, neural circuitry, and/or other neuroanatomy that affects activation of nerves and/or neurons. For example, neuromodulation (e.g., neurostimulation) can include one or more of the following effects on neural tissue: depolarizing the neurons such that the neurons fire action potentials; hyperpolarizing the neurons to inhibit action potentials; depleting neuron ion stores to inhibit firing action potentials; altering with proprioceptive input; influencing muscle contractions; affecting changes in neurotransmitter release or uptake; and/or inhibiting firing.

In some embodiments, disclosed here is a wearable neurostimulation device for transcutaneously stimulating one or more peripheral nerves of a user. The device can include, for example, any number of a plurality of electrodes configured to generate electric stimulation signals; and one or more hardware processors configured to: measure a plurality of distinct electromagnetic characteristics across the at least two electrodes; determine a plurality of connection quality indicators based on the measured plurality of electromagnetic characteristics, said connection quality indicators corresponding to a degree of connection between the at least two of the plurality of electrodes and skin of the user; update the plurality of connection quality indicators over a time window based on repeated measurements of the plurality of electromagnetic characteristics within the time window; determine that at least one of the plurality of connection quality indicators crosses a threshold within the time window; and/or change an operating characteristic of the wearable neurostimulation device based on the determination that the at least one of the plurality of connection quality indicators has crossed the threshold within the time window.

In some embodiments, the one or more hardware processors are configured to reset the plurality of connection quality indicators for a new time window.

In some embodiments, the one or more hardware processors are configured to maintain therapy during the time window where at least one of the plurality of connection quality indicators indicate a weak connection and where at least one of the plurality of connection quality indicators has not crossed the threshold.

In some embodiments, the electromagnetic characteristic comprises impedance.

In some embodiments, electromagnetic characteristic comprises voltage mismatch.

In some embodiments, the electromagnetic characteristic comprises a pulse shape In some embodiments, the operating characteristic includes stimulation settings.

In some embodiments, changing the operating characteristic includes generating an alert.

In some embodiments, each of the plurality of electromagnetic characteristics is configured to enable an independent determination of the connection quality indicator.

In some embodiments, disclosed herein is a method for monitoring the connection quality of a neurostimulation device. The method can include, for example, any number of the following: measuring a plurality of distinct electromagnetic characteristics across the at least two electrodes; determining a plurality of connection quality indicators based on the measured plurality of electromagnetic characteristics, said connection quality indicators corresponding to a degree of connection between the at least two of the plurality of electrodes and skin of the user; updating the plurality of connection quality indicators over a time window based on repeated measurements of the plurality of electromagnetic characteristics within the time window; determining that at least one of the plurality of connection quality indicators crosses a threshold within the time window; and changing an operating characteristic of the wearable neurostimulation device based on the determination that the at least one of the plurality of connection quality indicators has crossed the threshold within the time window.

In some embodiments, the method includes resetting the plurality of connection quality indicators for a new time window.

In some embodiments, the method includes maintaining therapy during the time window where at least one of the plurality of connection quality indicators indicate a weak connection and where at least one of the plurality of connection quality indicators has not crossed the threshold.

In some embodiments, the electromagnetic characteristic comprises impedance.

In some embodiments, the electromagnetic characteristic comprises voltage mismatch.

In some embodiments, the electromagnetic characteristic comprises a pulse shape determination.

In some embodiments, the operating characteristic includes stimulation settings.

In some embodiments, the changing the operating characteristic includes generating an alert.

In some embodiments, each of the plurality of electromagnetic characteristics is configured to enable an independent determination of the connection quality indicator.

In some embodiments, also disclosed herein is a wearable neurostimulation device for transcutaneously stimulating one or more peripheral nerves of a user. The device can include, for example, any number of the following: a plurality of electrodes configured to generate electric stimulation signals; and one or more hardware processors configured to: determine an electromagnetic characteristic across at least two of the plurality of electrodes; determine a connection quality indicator, corresponding to connection between the at least two of the plurality of electrodes and skin of the user, based on the determined electromagnetic characteristic; and/or change an operating characteristic of the wearable neurostimulation device based on the determined connection quality indicator.

In some embodiments, the electromagnetic characteristic comprises impedance.

In some embodiments, the electromagnetic characteristic comprises voltage mismatch.

In some embodiments, the electromagnetic characteristic comprises a pulse shape determination.

In some embodiments, the operating characteristic includes stimulation settings.

In some embodiments, the changing the operating characteristic includes generating an alert.

In some embodiments, the one or more hardware processors is configured to determine a plurality of electromagnetic characteristics across the at least two electrodes.

In some embodiments, each of the plurality of electromagnetic characteristics is configured to enable an independent determination of the connection quality indicator.

In some embodiments, the one or more hardware processors is configured to determine a plurality of connection quality indicators based on the determined plurality of electromagnetic characteristics.

In some embodiments, the one or more hardware processors is configured to track the determined plurality of connection quality indicators over a time period.

In some embodiments, the operating characteristic is only changed when at least one of the determined plurality of connection quality indicators exceed a threshold over the time period.

In some embodiments, disclosed herein is a wearable neurostimulation device for transcutaneously stimulating one or more peripheral nerves of a user. The device can include, for example, any number of the following: a plurality of electrodes configured to generate electric stimulation signals; and one or more hardware processors configured to: determine a plurality of electromagnetic characteristics across at least two of the plurality of electrodes; determine a plurality of connection quality indicators, corresponding to connection between the at least two of the plurality of electrodes and skin of the user, from each of the determined electromagnetic characteristic; track the plurality of connection quality indicators over a time window; and/or change an operating characteristic of the wearable neurostimulation device based on the tracking of the plurality of connection quality indicators.

In some embodiments, the plurality of electrodes comprise dry electrodes.

In some embodiments, the plurality of electrodes comprise a hydrogel.

In some embodiments, the plurality of electromagnetic characteristics comprise one or more of: impedance, voltage mismatch, and pulse shape determination.

In some embodiments, the one or more hardware processors is configured to track the plurality of connection quality indicators over a time window by maintaining one or more counters.

In some embodiments, the one or more hardware processors is configured to track the plurality of connection quality indicators over a time window by maintaining only a single counter based on the plurality of connection quality indicators.

In some embodiments, the one or more hardware processors is configured to change the operating characteristic of the wearable neurostimulation device if the plurality of connection quality indicators exceeds a threshold over the time window.

In some embodiments, the one or more hardware processors is configured to weight the plurality of connection quality indicators.

In some embodiments, the one or more hardware processors is configured to generate an alert to the patient.

In some embodiments, the one or more hardware processors is configured to change the operating characteristic of the wearable neurostimulation device by discontinuing stimulation.

In some embodiments, disclosed herein is a method for monitoring the connection quality of a neurostimulation device, that can include, for example, any number of the following: positioning a plurality of electrodes of the neurostimulation device on a skin of a user; delivering electrical stimulation transcutaneously through the plurality of electrodes; determining a plurality of electromagnetic characteristics across at least two of the plurality of electrodes; determining a plurality of connection quality indicators, corresponding to connection between the at least two of the plurality of electrodes and the skin of the user; tracking the plurality of connection quality indicators over a time window; and/or changing an operating characteristic of the wearable neurostimulation device if the plurality of connection quality indicators exceeds a threshold over the time window.

In some embodiments, the method includes determining a plurality of electromagnetic characteristics comprises determining one or more of: impedance, voltage mismatch, and pulse shape.

In some embodiments, tracking the plurality of connection quality indicators comprises maintaining at least one counter of connection quality over the time window based on the plurality of connection quality indicators.

In some embodiments, tracking the plurality of connection quality indicators comprises maintaining only a single counter of connection quality over the time window based on the plurality of connection quality indicators.

In some embodiments, the method includes initializing a value of the counter after the end of the time window.

In some embodiments, the method includes altering a value of the counter based on at least one of the plurality of connection quality indicators.

In some embodiments, changing the operating characteristic comprises discontinuing delivering the electrical stimulation, and/or modifying the delivered electrical stimulation.

In some embodiments, modifying the delivered electrical stimulation comprises changing one or more of the frequency, voltage, current, or duration of the stimulation.

In some embodiments, the method also includes alerting the user to an abnormality in the connection quality.

In some embodiments, disclosed herein is a wearable neuromodulation device for transcutaneously modulating one or more peripheral nerves of a user. The device can include, for example, any number of the following: a plurality of effectors configured to generate neuromodulation signals; and one or more hardware processors configured to: determine a characteristic across at least two of the plurality of effectors; determine a connection quality indicator, corresponding to connection between the at least two of the plurality of effectors and skin of the user, based on the determined characteristic; and/or change an operating characteristic of the wearable neuromodulation device based on the determined connection quality indicator.

In some embodiments, disclosed herein is a wearable neuromodulation device for transcutaneously modulating one or more peripheral nerves of a user. The device can include, for example, any number of the following: a plurality of effectors configured to generate neuromodulation signals; and one or more hardware processors configured to: determine a plurality of characteristic across at least two of the plurality of effectors; determine a plurality of connection quality indicators, corresponding to connection between the at least two of the plurality of effectors and skin of the user, from each of the determined electromagnetic characteristic; track the plurality of connection quality indicators over a time window; and/or change an operating characteristic of the wearable neuromodulation device based on the tracking of the plurality of connection quality indicators.

In some embodiments, disclosed herein is a wearable neuromodulation device for transcutaneously modulating one or more peripheral nerves of a user. The device can include, for example, any number of the following: a plurality of electrodes configured to generate electric stimulation signals; and one or more hardware processors configured to: measure one, two, three, four, five, or more distinct electromagnetic characteristics across the at least two electrodes; determine one, two, three, four, five, or more connection quality indicators based on the measured one or more electromagnetic characteristics, said connection quality indicators corresponding to a degree of connection between the at least two, three, four, five, or more of the plurality of electrodes and skin of the user; update the one, two, or more connection quality indicators over a time window based on repeated measurements of the one, two, three, four, five, or more electromagnetic characteristics within the time window; determine that one, two, three, four, five, or more of the connection quality indicators crosses a threshold within the time window; and/or change an operating characteristic of the wearable neurostimulation device based on the determination that the one, two, three, four, five, or more of the connection quality indicators has crossed the threshold within the time window.

In some embodiments, disclosed herein is a neuromodulation device according to any one of the embodiments described in the disclosure. A device can, in some embodiments, comprise, consist essentially of, consist of, and/or not comprise any number of features as disclosed herein.

In some embodiments, disclosed herein is a method for tracking one or more connection quality indicators according to any one of the embodiments described in the disclosure.

In some embodiments, disclosed herein is a method for changing an operating characteristic of a wearable neuromodulation device based on tracking of a plurality of connection quality indicators.

In several embodiments, the embodiments described herein that, for example, monitor the connection quality of a neuromodulation system can have one or more of the following advantages: (i) greater therapeutic benefit with less discomfort (e.g., such as from electrical discharge from open circuits); (ii) less current use (e.g., less power and improved battery life); (iii) decreased device error alerts and interruptions in therapy (and thus delays in completing a therapy session); (iv) increased likelihood of patient compliance due to the foregoing; and/or (v) improving the sensitivity in the determination of when to generate the alert and/or stop delivery of the electrical stimulation to balance the safety of users with efficacy and comfort.

In some of the embodiments described herein, one, several or all of the following features are not included: (i) sensors configured to assess patient motion and/or collect motion data, (ii) accelerometers, gyroscopes, magnetometers, inertial measurement units. and (iii) EMG or other muscle sensors. In some embodiments, systems and methods are not configured for, or are not placed on the upper arm and/or are not configured for neuromodulation on the skin surface of the forehead. In some embodiments, systems and methods are not configured to, or do not modulate descending (e.g., efferent) nerve pathways, and only modulate ascending (e.g., afferent) nerve pathways. In some embodiments, systems and methods are not configured to, or do not modulate nerves only on the ventral side of the wrist. In some embodiments, systems and methods do not include any implantable components. In some embodiments, systems and methods are not configured for percutaneous or subcutaneous stimulation, and are only configured for transcutaneous neuromodulation. In some embodiments, systems and methods are not configured for only neuromodulating, e.g., stimulating the ventral side of the wrist, rather some configurations may neuromodulate, e.g., deliver stimulation between two or more of the ventral, dorsal, and/or lateral sides of the wrist to target the medial nerve.

DETAILED DESCRIPTION

Figure 1A:
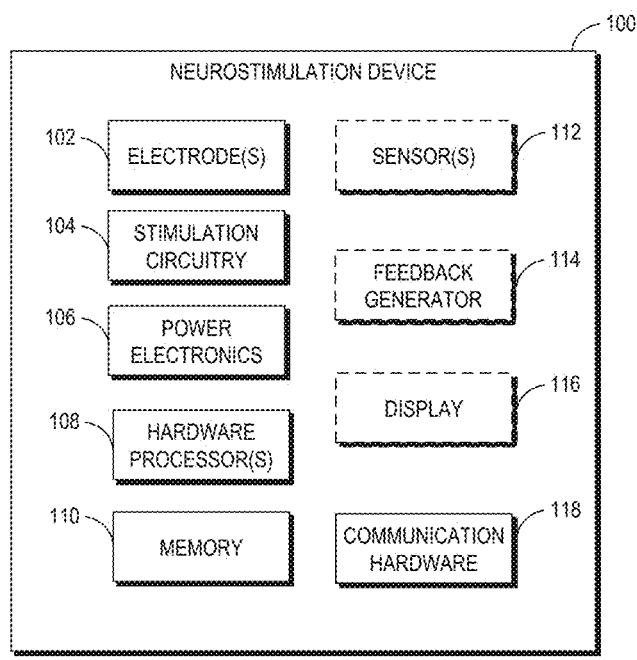
FIG. 1A illustrates a block diagram of an example neuromodulation (e.g., neurostimulation) device.

Several embodiments disclosed herein relate to systems and methods for neuromodulation, including for example devices configured for providing neurostimulation. The neuromodulation (e.g., neurostimulation) devices provided herein may be configured to stimulate peripheral nerves of a user. The devices may be configured to transcutaneously transmit one or more neuromodulation (e.g., neurostimulation) signals across the skin of the user. In many embodiments, the devices are wearable devices configured to be worn by a user. The user may be a human, another mammal, or other animal user. A neuromodulation (e.g., neurostimulation) system is also provided in several embodiments and includes signal processing systems and methods for enhancing diagnostic and therapeutic protocols relating to the same. In some embodiments, the neuromodulation (e.g., neurostimulation) device is configured to be wearable on an upper extremity of a user (e.g., a wrist, forearm, arm, and/or finger(s) of a user). In some embodiments, the device is configured to be wearable on a lower extremity (e.g., ankle, calf, knee, thigh, foot, and/or toes) of a user. In some embodiments, the device is configured to be wearable on the head or neck (e.g., forehead, ear, neck, nose, and/or tongue). In several embodiments, dampening or blocking of nerve impulses and/or neurotransmitters are provided. In some embodiments, nerve impulses and/or neurotransmitters are enhanced.

In some embodiments, the device is configured to be wearable on or proximate an ear of a user, including but not limited to auricular neuromodulation (e.g., neurostimulation) of the auricular branch of the vagus nerve, for example. The device could be unilateral or bilateral, including a single device or multiple devices connected with wires or wirelessly.

In some embodiments, the neuromodulation (e.g., neurostimulation) devices and methods disclosed herein generally rely on a robust connection with the skin of the user. In some embodiments, the electrode material conforms to the irregularities on the skin surface to ensure a robust and proper electrical connection. Conformance of the electrode to the skin surface can be affected by properties of the electrode, including but not limited to shape, thickness, material compliance (e.g., stiffness or durometer), and/or adhesion properties. Particularly, due to an application of electrical stimulation, an improper connection can result, for example, in current concentration that may make the device inoperable and/or may be harmful or painful to the user. For example, current concentrations can occur as an electrode lifts from the skin surface thus reducing the area of contact and, if current delivered by the device is held constant, increasing the current density. The connection quality may vary based on user movement. The connection state or quality between the skin and the effectors, e.g., electrode(s) may also depend on the type material used for the electrodes. In some instances, to improve the quality of user experience, especially for all day wear or multiple reapplications, the effectors, e.g., electrodes, may not include an adhesive hydrogel material. While an adhesive hydrogel layer can improve conformance with the skin, the stickiness of the hydrogel can be uncomfortable for the user or collect dust and debris during wear. This can sometimes increase the risk of poor connection quality. In some embodiments, the wearer is instructed to wet the wrist or electrodes with water, gel, lotion, or another conductive medium to improve the connection at the skin interface. Without a proper connection between the neuromodulation device and the user, the overall efficacy can be reduced in some embodiments due to improper delivery of electrical stimulation to the appropriate nerve targets or reduced adherence with the recommended usage due to discomfort or device errors (e.g., device not operating normally). Accordingly, some of the systems and methods described herein improve the efficacy of treatment by determining the connection quality between the device and the user. It has been observed that an increase in device errors may cause some users to not comply with their therapy regime due to either frustration with the device or possible reduction in therapeutic effect. Accordingly, in some embodiments, increased connection quality results in enhanced comfort for the user and reduce number of device disconnection errors, thus increasing compliance or adherence.

When the quality of the connection between the neuromodulation (e.g., neurostimulation) device and the user is poor, the device can be programmed to halt the stimulation to avoid improper delivery of electrical stimulation. The device can be further programmed to alert a user of the poor quality connection. However, there may be instances where false positives are generated. For example, connection may be poor only for a small time period while the user is moving and then stabilize. However, if alerts are constantly generated when the connection is poor, this may adversely affect user experience. Moreover, if the stimulation/modulation is halted every time when there is some indication of poor connection quality, it may reduce the efficacy of the treatment, and/or causes delays in completing a therapy session. Accordingly, the systems and methods described herein improve the sensitivity in the determination of when to generate the alert and/or stop delivery of the electrical stimulation to balance the safety of users with efficacy and comfort.

Neuromodulation Device

FIG. 1A illustrates a block diagram of an example neuromodulation (e.g., neurostimulation) device 100. The device 100 includes multiple hardware components which are capable of, or programmed to provide therapy across the skin of the user. As illustrated in FIG. 1A, some of these hardware components may be optional as indicated by dashed blocks. In some instances, the device 100 may only include the hardware components that are required for stimulation therapy. The hardware components are described in more detail below.

The device 100 can include two or more effectors, e.g. electrodes 102 for providing neurostimulation signals. In some instances, the device 100 is configured for transcutaneous use only and does not include any percutaneous or implantable components. In some embodiments, the electrodes can be dry electrodes. In some embodiments, water or gel can be applied to the dry electrode or skin to improve conductance. In some embodiments, the electrodes do not include any hydrogel material, adhesive, or the like. The electrodes 102 can also be used to determine a connection quality as discussed below.

The device 100 can further include stimulation circuitry 104 for generating signals that are applied through the electrode(s) 102. The signals can vary in frequency, phase, timing, amplitude, or offsets. The device 100 can also include power electronics 106 for providing power to the hardware components. For example, the power electronics 106 can include a battery.

The device 100 can include one or more hardware processors 108. The hardware processors 108 can include microcontrollers, digital signal processors, application specific integrated circuit (ASIC), a field programmable gate array (FPGA) or other programmable logic device, discrete gate or transistor logic, discrete hardware components, or any combination thereof designed to perform the functions described herein. In an embodiment, all of the processing discussed herein is performed by the hardware processor(s) 108. The memory 110 can store data specific to patient and rules as discussed below.

In the illustrated figure, the device 100 can include one or more sensors 112. As shown in the figure, the sensor(s) 112 may be optional. Sensors could include, for example, biomechanical sensors configured to, for example, measure motion, and/or bioelectrical sensors (e.g., EMG, EEG, and/or nerve conduction sensors). Sensors can include, for example, cardiac activity sensors (e.g., ECG, PPG), skin conductance sensors (e.g., galvanic skin response, electrodermal activity), and motion sensors (e.g., accelerometers, gyroscopes). The one or more sensors 102 may include an inertial measurement unit (IMU).

In some embodiments, the IMU can include one or more of a gyroscope, accelerometer, and magnetometer, which may also be used to determine connection quality. The IMU can be affixed or integrated with the neuromodulation (e.g., neurostimulation) device 100. In an embodiment, the IMU is an off the shelf component. In addition to its ordinary meaning, the IMU can also include specific components as discussed below. For example, the IMU can include one more sensors capable of collecting motion data. In an embodiment, the IMU includes an accelerometer. In some embodiments, the IMU can include multiple accelerometers to determine motion in multiple axes. Furthermore, the IMU can also include one or more gyroscopes and/or magnetometer in additional embodiments. Since the IMU can be integrated with the neurostimulation device 100, the IMU can generate data from its sensors responsive to motion, movement, or vibration felt by the device 100. Furthermore, when the device 100 with the integrated IMU is worn by a user, the IMU can enable detection of voluntary and/or involuntary motion of the user.

The device 100 can optionally include user interface components, such as a feedback generator 114 and a display 116. The display 116 can provide instructions or information to users relating to calibration or therapy. The display 116 can also provide alerts, such an indication of poor connection quality or band not connected. Alerts may also be provided using the feedback generator 114, which can provide haptic feedback to the user, such as upon initiation or termination of stimulation, for reminder alerts, to alert the user of a troubleshooting condition such as connection quality, to perform a tremor inducing activity to measure tremor motion, among others. Accordingly, the user interface components, such as the feedback generator 114 and the display 116 can provide audio, visual, and haptic feedback to the user.

Furthermore, the device 100 can include communications hardware 118 for wireless or wired communication between the device 100 and an external system, such as the user interface device discussed below. The communications hardware 118 can include an antenna. The communications hardware 118 can also include an Ethernet or data bus interface for wired communications.

While the illustrated figure shows several components of the device 100, some of these components are optional and not required in all embodiments of the device 100. In some embodiments, a system can include a diagnostic device or component that does not include neuromodulation functionality. The diagnostic device could be a companion wearable device connected wirelessly through a connected cloud server, and include, for example, sensors such as cardiac activity, skin conductance, and/or motion sensors as described elsewhere herein.

In some embodiments, the device 100 can also be configured to deliver one, two or more of the following: magnetic, vibrational, mechanical, thermal, ultrasonic, or other forms of stimulation instead of, or in addition to electrical stimulation. Such stimulation can be delivered via one, two, or more effectors in contact with, or proximate the skin surface of the patient. However, in some embodiments, the device is configured to only deliver electrical stimulation, and is not configured to deliver one or more of magnetic, vibrational, mechanical, thermal, ultrasonic, or other forms of stimulation.

Although several neurostimulation devices are described herein, in some embodiments nerves are modulated non-invasively to achieve neuro-inhibition. Neuro-inhibition can occur in a variety of ways, including but not limited to hyperpolarizing the neurons to inhibit action potentials and/or depleting neuron ion stores to inhibit firing action potentials. This can occur in some embodiments via, for example, anodal or cathodal stimulation, low frequency stimulation (e.g., less than about 5 Hz in some cases), or continuous or intermediate burst stimulation (e.g., theta burst stimulation). In some embodiments, the wearable devices have at least one implantable portion, which may be temporary or more long term. In many embodiments, the devices are entirely wearable and non-implantable.

User Interface Device

Figure 1B:
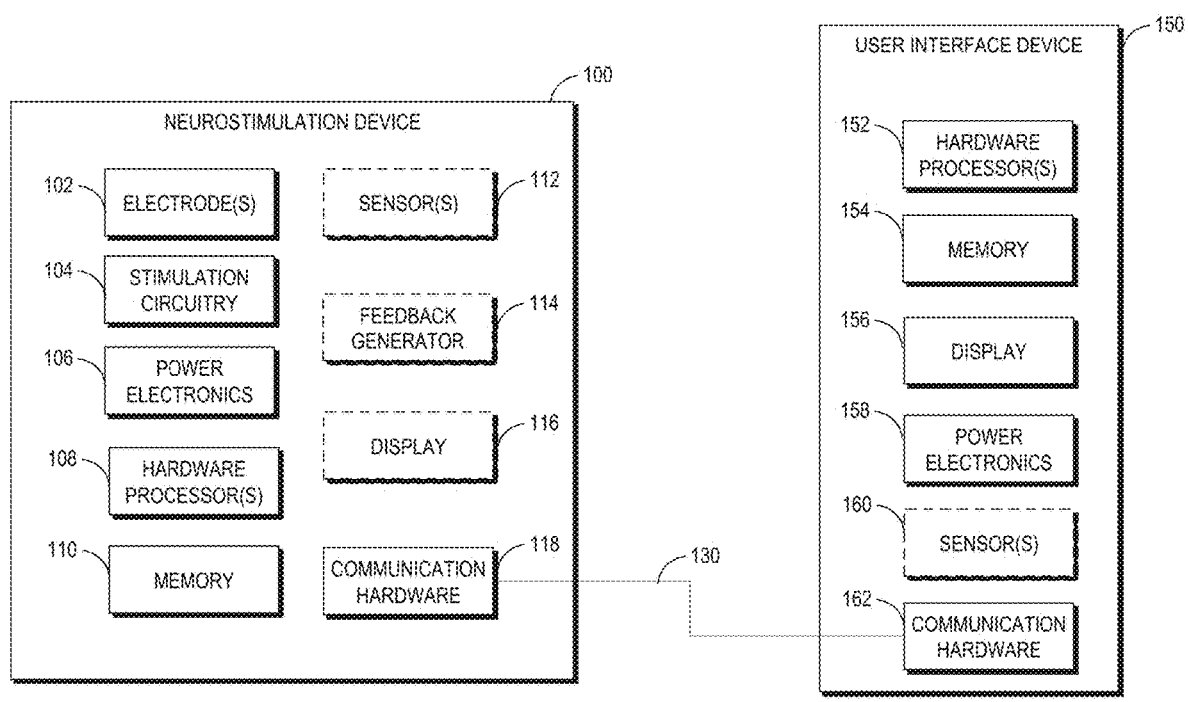
FIG. 1B illustrates a block diagram of an embodiment of a controller that can be implemented with the hardware components described with respect to FIG. 1A.

FIG. 1B illustrates communications between the neurostimulation device 100 and a user interface device 150 over a communication link 130. The communication link 130 can be wired or wireless. The neuromodulation (e.g., neurostimulation) device 100 is capable of communicating and receiving instructions from a user interface device 150. The user interface device 150 can include a computing device. In some embodiments, the user interface device 150 is a mobile computing device, such as a mobile phone, a smartwatch, a tablet, or a wearable computer. The user interface device 150 can also include server computing systems that are remote from the neurostimulation device. The user interface device 150 can include hardware processor(s) 152, a memory 154, display 156, and power electronics 158. In some embodiments, a user interface device 150 can also include one or more sensors, such as sensors described elsewhere herein. Furthermore, in some instances, the user interface device 150 can generate an alert responsive to connection quality between the electrodes and skin of the patient. The alert may be received from the neurostimulation device 100.

In additional embodiments, data acquired from the one or more sensors 102 is processed by a combination of the hardware processor(s) 108 and hardware processor(s) 152. In further embodiments, data collected from one or more sensors 102 is transmitted to the user interface device 150 with little or no processing performed by the hardware processors 108. In some embodiments, the user interface device 150 can include a remote server that processes data and transmits signals back to the device 100 (e.g., via the cloud).

Controller

Figure 1C:
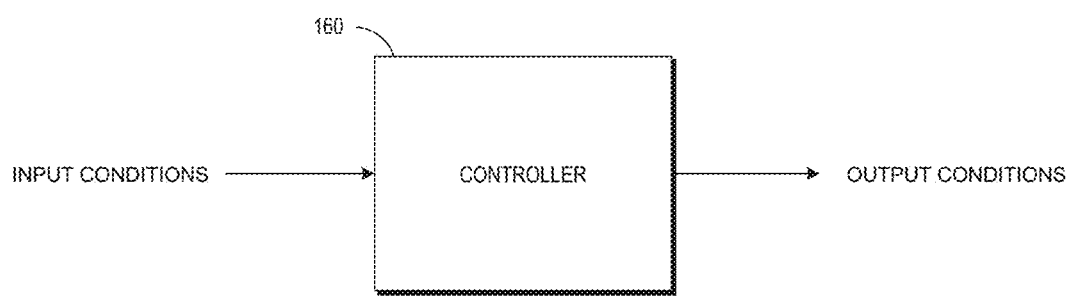
FIG. 1C illustrates a block diagram of an embodiment of a controller.

FIG. 1C illustrates a block diagram of an embodiment of a controller 160. The controller 160 can include one or more software engines for performing the processes and functions described herein. The software engines can include programmed instructions for performing processes as discussed herein (and illustrated in flowcharts) for detection of input conditions and control of output conditions based on determination of connection quality. The engines can be executed by the one or more hardware processors of the neurostimulation device 100 alone or in combination with the user interface device 150. The programming instructions can be stored in a memory 110. The programming instructions can be implemented in C, C++, JAVA, or any other suitable programming languages. In some embodiments, some or all of the portions of the controller 200 including the engines can be implemented in application specific circuitry such as ASICs and FPGAs. Some aspects of the functionality of the controller 200 can be executed remotely on a server (not shown) over a network. Accordingly, the controller 160 can be implemented with the hardware components described above with respect to FIG. 1A.

Impedance Determination

Figure 2:
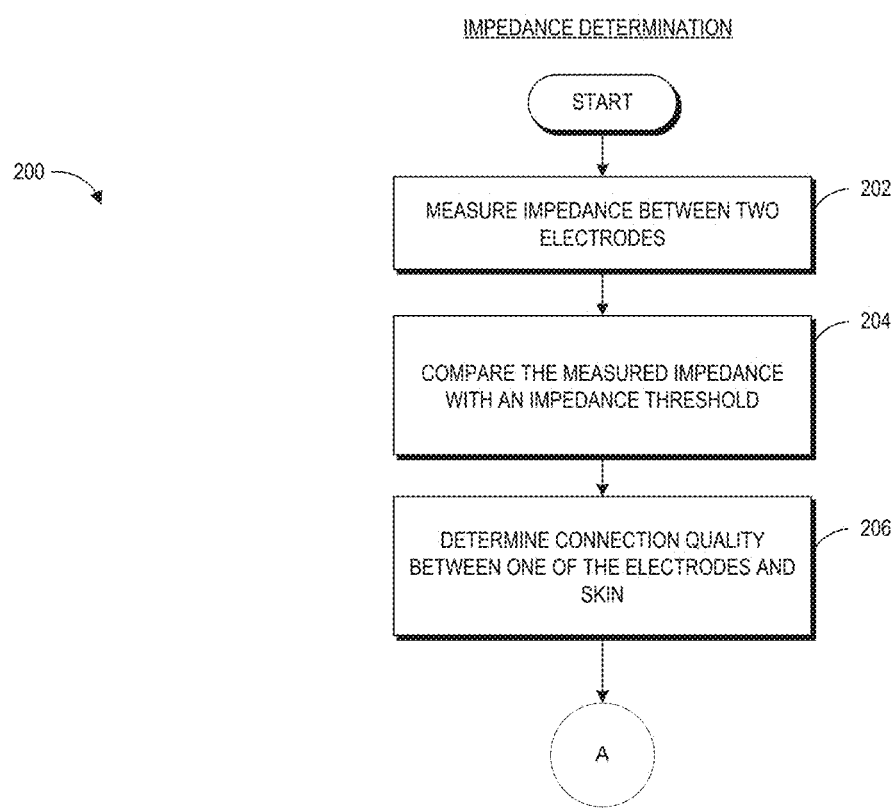
FIG. 2 illustrates a flow chart of an embodiment of a process for determination of connection quality using impedance determination.

FIG. 2 illustrates a flowchart of an example process 200 for determining connection quality using impedance. The process 200 can be implemented by any of the systems discussed above. The process 200 can be implemented alone or in combination with other processes described below.

The impedance determination process 200 can begin at block 202 with measuring impedance between any two electrodes of the neurostimulation device 100. The determination of impedance can indicate a presence of an open circuit. For example, when there is a poor connection between the electrodes and the skin, the impedance value may be high, corresponding to an open circuit. Such high impedance can result in an improper delivery of electrical stimulation, such as an increase in current density. Accordingly, the impedance measurement can be used to determine connection quality between the electrodes and the skin. In some instances, impedance can be measured for some or all pairs of the electrodes 102.

At block 204, the controller 160 can compare the measured impedance with an impedance threshold value. This threshold value might be stored in the memory 110. Based on the comparison, the controller 160 can determine connection quality between the electrodes and the skin of the patient. The impedance for a skin is generally about 4 kΩ. The threshold value can be a factor of the general skin impedance. Example values include about, at least about, or no more than about 8 kΩ, 20 kΩ, 40 kΩ, 50 kΩ, or about 100 kΩ, or ranges including any two of the foregoing values. In some instances, the threshold value is at least about 4 kΩ. If the comparison indicates an open circuit condition, the controller 160 can set connection quality to be low or poor. The connection quality can be a numeric indicator. The numeric indicator can represent a degree of quality of connection. In some instances, the connection quality can be a binary indicator, indicating true (1) or false (0) for whether the connection quality is good or bad. The connection quality can also be a textual indicator, such as "Band Not Connected." The connection quality indicator can be used by the controller 160 to determine output conditions as discussed in more detail below with respect to FIG. 5. Output conditions can include alerts and/or control of the neurostimulation device 100. For example, output conditions can include halting the stimulation, changing a characteristic of the stimulation, or maintaining a current stimulation treatment. In some instances, the controller 160 can use the impedance detection process 200 by itself to determine the connection quality indicator and control output conditions.

Pulse Shape Determination

Figure 3:
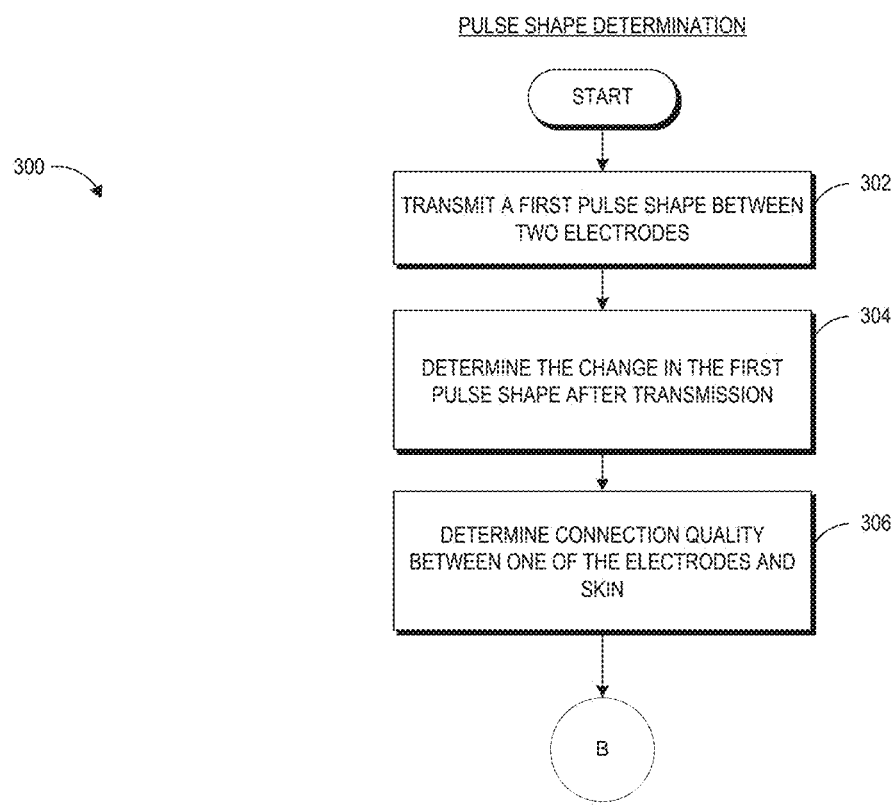
FIG. 3 illustrates a flow chart of an embodiment of a process for determination of connection quality using pulse shape determination.

FIG. 3 illustrates a flowchart of an example process 300 for determining connection quality using pulse shape. The process 300 can be implemented by any of the systems discussed above. The process 300 can be implemented alone or in combination with other processes described herein, such as the impedance determination process 200.

The pulse shape determination process 300 can begin at block 302 with a transmission of a pulse having a particular shape across any two electrodes of the neurostimulation device 100. In some instances, the pulse shape can correspond to a positive pulse. In other instances, the pulse shape can correspond to a negative pulse. In other instances, the pulse shape can correspond to a positive and a negative pulse, with an interpulse interval. The pulse shape can also be gaussian or any other profile. The controller 160 can use predetermined pulse shapes stored in the memory 110. The controller 160 can cause the transmission of the pulse at block 302.

When the connection quality is poor, the pulse shape is distorted as it is transmitted across the electrodes. Higher distortion generally corresponds to poor quality connection. Accordingly, the controller 160 can determine the change in the profile of the pulse that was transmitted. In some instances, the change is determined based on the area under the curve of the received pulse. In some instances, the change is determined based on features of the pulse in the time domain, such pulse width or pulse amplitude. The change may also be determined based on a phase of the waveform. Further, the change may also be determined based on duration or time points of wave shape. The change can also be determined based on cross-correlation of the transmitted and received pulse or any other suitable signal processing techniques. In some instances, about or at least about 10%, 15%, 20%, 25%, 30%, or more change in pulse shape or pulse shape features is used as a threshold to determine connection quality indicator. Other values of thresholds can be used to adjust sensitivity.

Based on the change in pulse profile, the controller 160 can determine the connection quality between the electrodes and the skin at block 306. As discussed above, the connection quality can be a numeric, binary, or a textual indicator. The connection quality indicator can be used by the controller 160 to determine output conditions as discussed in more detail below with respect to FIG. 5. In some instances, the controller 160 can use the pulse shape determination process 300 by itself to determine the connection quality indicator and control output conditions.

Voltage Mismatch Determination

Figure 4:
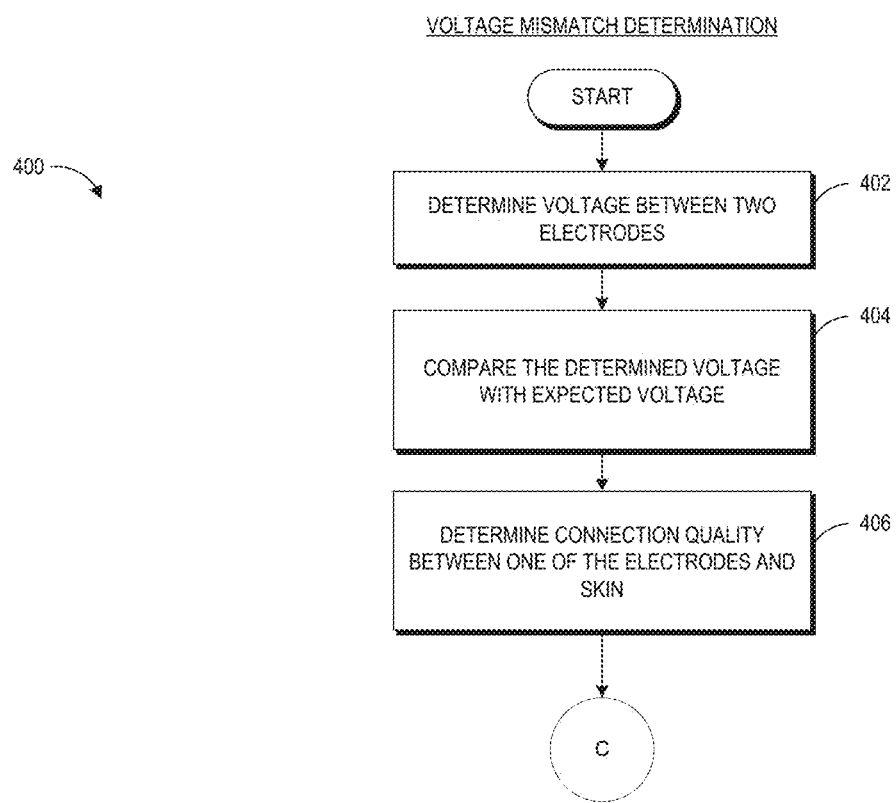
FIG. 4 illustrates a flow chart of an embodiment of a process for determination of connection quality using voltage mismatch.

FIG. 4 illustrates a flowchart of an example process 400 for determining connection quality using voltage mismatch. The process 400 can be implemented by any of the systems discussed above. The process 400 can be implemented alone or in combination with other processes described herein, such as the impedance determination process 200 and/or the pulse shape determination process 300.

In several embodiments, the pulse shape determination process 400 can begin at block 402 with a determination of voltage across any two electrodes of the neurostimulation device 100. In some instances, the controller 160 can test the voltage difference across two electrodes. The actual voltage measured can be a function of connection quality between the electrodes and skin. If the connection quality is good, the actual voltage measured will be close to the expected value. In contrast, for a poor quality connection the actual voltage may deviate from the expected value. Accordingly, the controller 160 can compare the measured voltage with the expected voltage at block 404. Example values of thresholds for the voltage difference include about 5 k mV, about 10 k mV, about 50 k mV, about 70 k mV, and about 100 k mV or more or less, or ranges including any two of the foregoing values.

Based on the comparison, the controller 160 can determine an indication of connection quality between the electrodes and the skin at block 406. In some instances, the controller 160 can use the voltage mismatch determination process 300 by itself to determine the connection quality indicator and control output conditions.

Connection Quality Indicator Determination

Figure 5A:
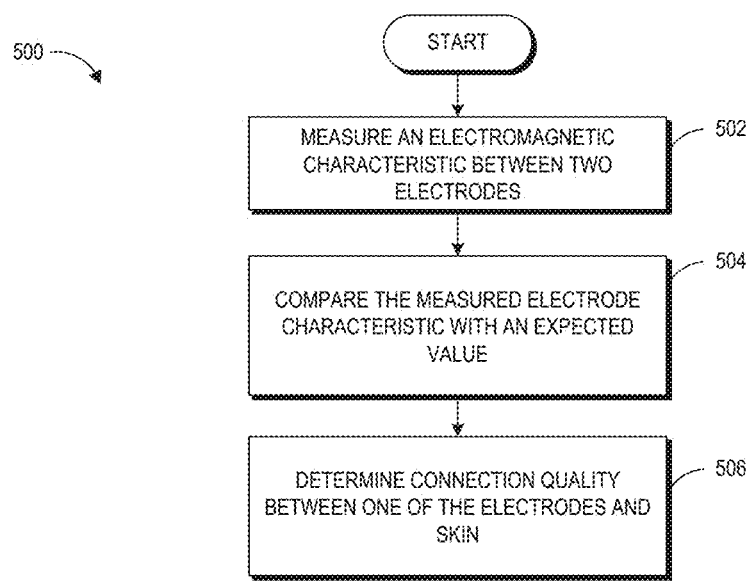
FIG. 5A illustrates a flow chart of an embodiment of a process for determination of connection quality.

FIG. 5A illustrates an example process 500 for determination of connection quality indicator. The process 500 can be implemented by any of the systems described above. The process 500 can incorporate any of the processes discussed above with respect to FIGS. 2 to 4.

That is, at block 502, the controller 160 can measure an electromagnetic characteristic between two electrodes. The electromagnetic characteristic can include voltage mismatch, impedance determination, or pulse shape determination as discussed above. In some embodiments, the electromagnetic characteristic does not include one or more of voltage mismatch, impedance determination, or pulse shape determination. Other electromagnetic characteristics can include signal quality of delivered current, including but not limited to signal to noise ratio.

At block 504, the controller 160 can compare the measured electrode characteristic with an expected value. For example, the controller 160 can compare the measured values with stored thresholds to identify an open circuit, or pulse shape distortion, or voltage mismatch as discussed above.

Based on the comparison, the controller 160 can determine connection quality indicator between one of the electrodes and skin of the patient at block 506. As discussed above, the connection quality indicator can be a numeric, binary, or a textual indicator. The connection quality indicator can be used by the controller 160 to determine output conditions. Output conditions can include alerts and/or control of the neurostimulation device 100. Alerts can include haptic feedback, visual display, and halting stimulation. For example, output conditions can include halting the stimulation, changing a characteristic of the stimulation, or maintaining current stimulation treatment.

Accumulation Dissipation (AD) Determination

Figure 5B:
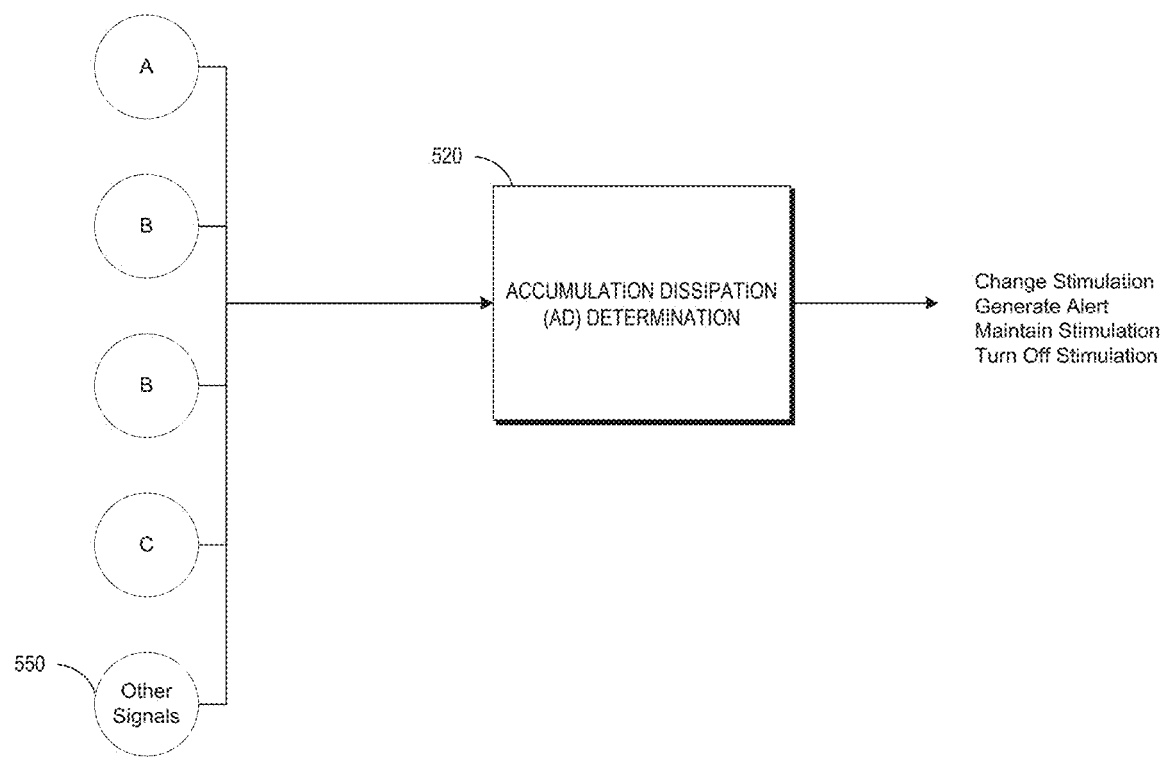
FIG. 5B illustrates an architecture for determination of connection quality using more than one of the processes over time.

The controller 160 can use any of the processes 200, 300, or 400 discussed above individually or in combination to determine connection quality and control output conditions. However, changing an output condition based on the determination of the connection quality from one of the processes instantaneously or relative instantaneously can result in false alarms or unnecessarily high sensitivity to connection condition. FIG. 5B illustrates an architecture for combining the processes 200, 300, and 400 and adding a time component (or persistence) with the AD determination 520 (discussed in detail with respect to FIG. 5C) before executing a change the output condition.

The AD determination 520 can use outputs from some or all of the processes described above as shown in FIG. 5B. The outputs may be weighted equally or unequally. In some instances, the AD determination 520 can receive outputs from multiple pulse shape determinations processes 300, each including a different pulse shape. In one example, the AD determination 500 uses a positive pulse and a negative pulse as the transmitted pulses in the pulse shape determinations processes 400. The AD determination 520 can also use other signals 550 to determine output conditions. For example, the accelerometer data from IMU 102 can be used the by controller 160 to determine sudden movements by the user. The controller 160 can correlate the movement data with the connection quality indicator data received from one of the processes discussed above. Other signals 550 can also include user inputs indicating their preference on connection quality threshold and when to change the output conditions.

The output conditions can include, for example, generating an alert, changing neuromodulation (e.g., stimulation) properties, halting the neuromodulation (e.g., stimulation), or maintaining neuromodulation (e.g., stimulation). The time component will be described below with respect to FIG. 5C.

Figure 5C:
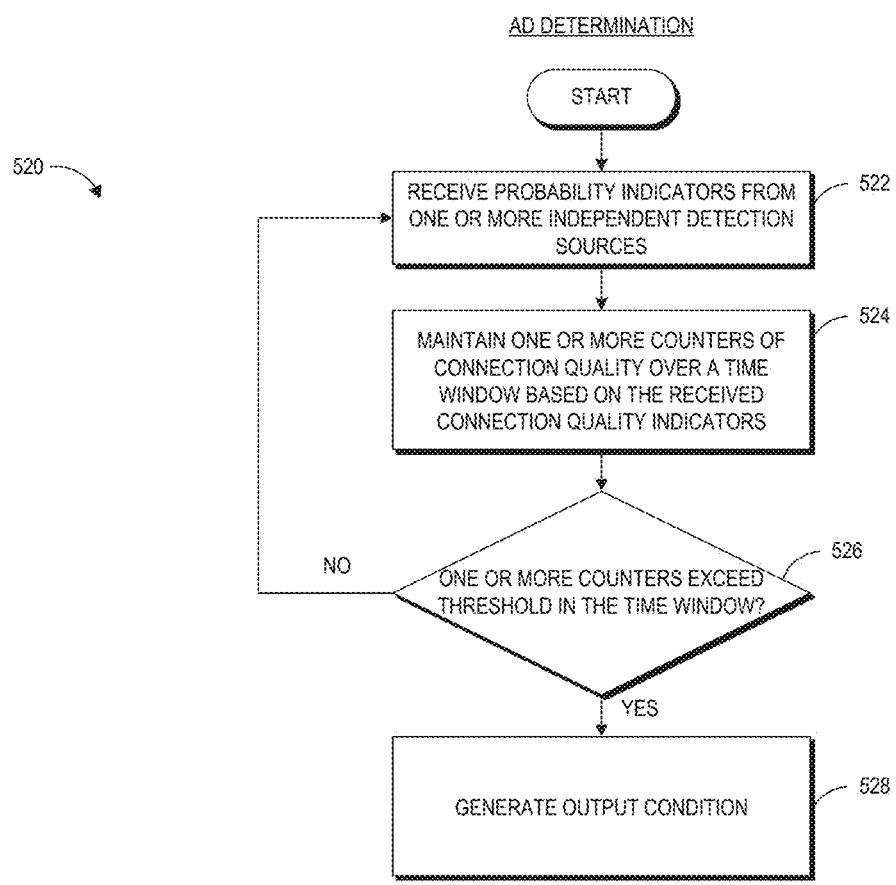
FIG. 5C illustrates a flow chart of an embodiment of a process for adding a time component to the processes discussed above.

FIG. 5C illustrates a flowchart of an example process 520 for AD determination that adds time component to the processes discussed above. The process 520 can be implemented by any of the systems discussed above.

At block 522, the controller 160 can receive connection quality indicators from the one or more processes 200-400 discussed above. In some examples, as illustrated in block 524, the controller 160 can maintain one or more counters in the memory 110 corresponding to overall connection quality based on the received connection quality indicators from each of the processes shown in FIG. 5A. In one example, a single counter is used by the controller 160 to determine overall connection quality. When one of the processes 200-400 as shown in FIG. 5A indicates a poor connection quality, the controller 160 can increase the counter by 1. If one of the processes outputs a good connection quality indicator, the counter can be decreased by 1. The poor and good are relative terms. As discussed above, the connection quality indicators can be numeric, binary, or textual. While the counters are described in terms of integers and changing in a particular direction, this is relative and other means for tracking can be used.

In some instances, the controller 160 can maintain separate counters for each of the processes illustrated in FIG. 5A. That is, whenever a connections quality indicator is good or bad for a respective process, the respective counter for that process is increased or decreased accordingly by the controller 160. These counters can be stored in the memory 110.

At block 526, the controller 160 can compare the one or more counters to respective one or more threshold. If a single counter is used, the controller 160 compares the single counter with the threshold. When the counter exceeds a threshold, the controller 160 can generate an output condition as shown in block 528. If multiple counters are used, such as a counter for each of the processes input, the controller 160 can compare each of these counters with its respective threshold value. In one example, if any one of the counters exceed their respective threshold, the controller 160 can generate an output condition as shown in block 508. If the counters are within their limits, the controller 160 can continue monitoring the connection quality. In some instances, the controller 160 can poll one or more processes discussed above in a loop at regular intervals. Further, in some examples, the processes can run in parallel and send an indication at regular intervals.

In some instances, the time window is 125 milliseconds, 250 milliseconds, or 500 milliseconds, or more or less. The one or more counters may be initialized to zero at the start of a new time period. The time window can also be continuous. Thus, in some instances, the counters are not initialized after any particular time and maintained throughout the therapy time. Furthermore, in some cases, the threshold count is 64. In other examples, the threshold count can be 128 or higher. In additional examples, the threshold count can be less than 64, between about 32 and 512, or about 32, 64, 128, 256, 512, or ranges including any two of the foregoing values. The users may also be able to set threshold count based on their preferences. Output condition can include changing properties of the stimulation (for example, frequency, voltage, current, duration); halting the stimulation, or generating an alert that can be visual, auditory, or haptic.

Thus, based on the AD determination 520, the controller 160 can adjust or tune when to change the output or operating condition of the neurostimulation device 100 to balance between safety and efficacy. The threshold counts, like threshold values discussed above, can be adjusted to change sensitivity. For example, increasing the threshold count can make the neurostimulation device 100 less sensitive to connection quality errors, while decreasing the threshold count can make the neurostimulation device 100 more sensitive to connection quality errors. In some instances, the threshold counts and values can be set externally by a hospital or manufacturer and can be updated remotely.

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. References to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately." even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. The methods disclosed herein include certain actions taken by a practitioner; however, they can also include any third-party instruction of those actions, either expressly or by implication. For example, actions such as "percutaneously stimulating an afferent peripheral nerve" includes "instructing the stimulation of an afferent peripheral nerve."

What is claimed is:

1. A wearable neurostimulation device for transcutaneously stimulating one or more peripheral nerves of a user, the device comprising:
   circuitry for generating electric stimulation signals;
   a plurality of electrodes configured to emit the electric stimulation signals; and
   one or more hardware processors configured to:
      measure a plurality of electromagnetic characteristics across at least two of the plurality of electrodes,
      wherein the at least two of the plurality of electrodes comprises a first electrode and a second electrode,
      wherein the plurality of electromagnetic characteristics comprises a first electromagnetic characteristic of the first electrode, and
      wherein the plurality of electromagnetic characteristics comprises a second electromagnetic characteristic of the second electrode;
      determine a plurality of connection quality indicators based on the first electromagnetic characteristic and the second electromagnetic characteristic, said connection quality indicators corresponding to a degree of connection between the first electrode and the second electrode with skin of the user;
      maintain one or more counters for the plurality of connection quality indicators over a time window based on repeated measurements of the plurality of electromagnetic characteristics within the time window;
      wherein maintaining one or more counters for the plurality of connection quality indicators comprises determining if at least one of the one or more counters crosses a threshold within the time window; and
      change an operating characteristic of the wearable neurostimulation device if at least one of the one or more counters has crossed the threshold within the time window;
      wherein the one or more hardware processors are capable of determining the plurality of connection quality indicators based on the plurality of electromagnetic characteristics.

2. The wearable neurostimulation device of claim 1, wherein the one or more hardware processors are configured to reset the one or more counters after the time window has elapsed.

3. The wearable neurostimulation device of claim 1, wherein the one or more hardware processors are configured to maintain therapy during the time window where at least one of the plurality of connection quality indicators indicate a weak connection and where at least one of the plurality of connection quality indicators has not crossed the threshold.

4. The wearable neurostimulation device of claim 1, wherein the electromagnetic characteristic comprises impedance.

5. The wearable neurostimulation device of claim 1, wherein the electromagnetic characteristic comprises voltage mismatch.

6. The wearable neurostimulation device of claim 1, wherein the electromagnetic characteristic comprises a pulse shape determination.

7. The wearable neurostimulation device of claim 1, wherein the operating characteristic includes stimulation settings.

8. The wearable neurostimulation device of claim 1, wherein the changing the operating characteristic includes generating an alert.

9. The wearable neurostimulation device of claim 1, wherein each of the plurality of electromagnetic characteristics is configured to enable an independent determination of the connection quality indicator independent of at least one other determination of the connection quality indicator.

10. A wearable neurostimulation device for transcutaneously stimulating one or more peripheral nerves of a user, the device comprising:
    circuitry for generating electric stimulation signals;
    a plurality of electrodes configured to emit the electric stimulation signals; and
    one or more hardware processors configured to:
       determine a first electromagnetic characteristic across a first electrode of the plurality of electrodes and a second electromagnetic characteristic across a second electrode of the plurality of electrodes;
       determine a first connection quality indicator, corresponding to connection between the first electrode of the plurality of electrodes and skin of the user, based on the determined electromagnetic characteristic;
       determine a second connection quality indicator, corresponding to connection between the second electrode of the plurality of electrodes and skin of the user, based on the determined electromagnetic characteristic;

maintain a first counter corresponding to the first connection quality indicator over a time window, wherein the first counter can increase or decrease during the time window based on the connection quality indicator;

maintain a second counter corresponding to the second connection quality indicator over a time window, wherein the first counter can increase or decrease during the time window based on the connection quality indicator; and change an operating characteristic of the wearable neurostimulation device based on either the first counter or the second counter exceeding a threshold.

11. The wearable neurostimulation device of claim 10, wherein the electromagnetic characteristic comprises impedance.

12. The wearable neurostimulation device of claim 10, wherein electromagnetic characteristic comprises voltage mismatch.

13. The wearable neurostimulation device of claim 10, wherein electromagnetic characteristic comprises a pulse shape determination.

14. The wearable neurostimulation device of claim 10, wherein the operating characteristic includes stimulation settings.

15. The wearable neurostimulation device of claim 10, wherein the changing the operating characteristic includes generating an alert.

16. The wearable neurostimulation device of claim 10, wherein the one or more hardware processors is configured to determine a plurality of electromagnetic characteristics across the plurality of electrodes, wherein each of the plurality of electromagnetic characteristics is configured to enable an independent determination of the connection quality indicator.

17. The wearable neurostimulation device of claim 16, wherein the one or more hardware processors is configured to determine a plurality of connection quality indicators based on the determined plurality of electromagnetic characteristics.

18. The wearable neurostimulation device of claim 17, wherein the one or more hardware processors is configured to track the determined plurality of connection quality indicators over a time period.

19. The wearable neurostimulation device of claim 18, wherein the operating characteristic is only changed when at least one of the determined plurality of connection quality indicators exceed a threshold over the time period.

* * * * *